US010465113B2

(12) United States Patent
Sudo et al.

(10) Patent No.: US 10,465,113 B2
(45) Date of Patent: Nov. 5, 2019

(54) NEMATIC LIQUID CRYSTAL COMPOSITION, AND LIQUID CRYSTAL DISPLAY ELEMENT MANUFACTURED USING SAME

(71) Applicant: DIC Corporation, Tokyo (JP)

(72) Inventors: Go Sudo, Kita-adachi-gun (JP); Shinichi Hirata, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 93 days.

(21) Appl. No.: 15/547,964

(22) PCT Filed: Apr. 14, 2016

(86) PCT No.: PCT/JP2016/061999
§ 371 (c)(1),
(2) Date: Aug. 1, 2017

(87) PCT Pub. No.: WO2016/171064
PCT Pub. Date: Oct. 27, 2016

(65) Prior Publication Data
US 2018/0030346 A1 Feb. 1, 2018

(30) Foreign Application Priority Data
Apr. 24, 2015 (JP) ................................ 2015-089433

(51) Int. Cl.
*G02F 1/1333* (2006.01)
*C09K 19/14* (2006.01)
*C07C 15/18* (2006.01)
*C07C 25/13* (2006.01)
*C07C 25/18* (2006.01)
*C09K 19/12* (2006.01)
*C09K 19/30* (2006.01)
*C09K 19/54* (2006.01)
*C09K 19/32* (2006.01)
*G02F 1/137* (2006.01)

(52) U.S. Cl.
CPC .............. *C09K 19/14* (2013.01); *C07C 15/18* (2013.01); *C07C 25/13* (2013.01); *C07C 25/18* (2013.01); *C09K 19/12* (2013.01); *C09K 19/3028* (2013.01); *C09K 19/3066* (2013.01); *C09K 19/322* (2013.01); *C09K 19/542* (2013.01); *C09K 2019/122* (2013.01); *C09K 2019/3004* (2013.01); *C09K 2019/3009* (2013.01); *C09K 2019/3016* (2013.01); *C09K 2019/325* (2013.01); *C09K 2019/548* (2013.01); *G02F 2001/13712* (2013.01)

(58) Field of Classification Search
CPC .... C09K 19/14; C09K 19/12; C09K 19/3028; C09K 19/3066; C09K 19/322; C09K 19/542; C09K 2019/122; C09K 2019/3004; C09K 2019/3009; C09K 2019/3016; C09K 2019/325; C09K 2019/548; G02F 1/1333; G02F 2001/13712
USPC ..................................................... 252/299.63
See application file for complete search history.

(56) References Cited

U.S. PATENT DOCUMENTS

| 5,599,480 | A | 2/1997 | Tarumi et al. |
| 6,190,576 | B1 | 2/2001 | Andou et al. |
| 6,576,303 | B1 | 6/2003 | Tamura et al. |
| 9,359,553 | B2* | 6/2016 | Saito ........................ C07C 13/28 |
| 2002/0030179 | A1 | 3/2002 | Miyazawa et al. |
| 2004/0065866 | A1 | 4/2004 | Kato et al. |
| 2006/0238696 | A1 | 10/2006 | Wen et al. |
| 2015/0240160 | A1 | 8/2015 | Saito et al. |
| 2016/0237347 | A1 | 8/2016 | Sudo et al. |

FOREIGN PATENT DOCUMENTS

| JP | 8-104869 | A | 4/1996 |
| JP | 2000-53602 | A | 2/2000 |
| JP | 2004-115475 | A | 4/2004 |
| JP | 2006-301643 | A | 11/2006 |
| JP | 2013-208201 | A | 10/2013 |
| JP | 2015-178591 | A | 10/2015 |
| WO | 97/036847 | A1 | 10/1997 |
| WO | 99/021816 | A1 | 5/1999 |

(Continued)

OTHER PUBLICATIONS

International Search Report dated Jul. 5, 2016, issued in counterpart International Application No. PCT/JP2016/061999 (2 pages).

(Continued)

*Primary Examiner* — Geraldina Visconti
(74) *Attorney, Agent, or Firm* — Westerman, Hattori, Daniels & Adrian, LLP

(57) ABSTRACT

The present invention is a liquid crystal composition having negative dielectric anisotropy containing one or two or more of compounds represented by General Formula (i), and is also a liquid crystal display element using the liquid crystal composition. The problem to be solved by the present invention is to provide a liquid crystal composition with a large refractive index anisotropy ($\Delta n$), a low rotational viscosity ($\gamma_1$), a large elastic constant ($K_{33}$), a high voltage holding ratio (VHR), and which has a negative dielectric anisotropy ($\Delta \varepsilon$), and a liquid crystal display element which, when using the liquid crystal composition, has a high response speed with excellent display quality in which display defects such as drop marks, burn-in, and display unevenness are absent or suppressed.

15 Claims, No Drawings

(56) References Cited

FOREIGN PATENT DOCUMENTS

| WO | 00/039063 A1 | 7/2000 |
| WO | 2015/050035 A1 | 4/2015 |

OTHER PUBLICATIONS

Notification of Reasons for Refusal dated Nov. 22, 2016, issued in counterpart Japanese Patent Application No. 2016-559667, w/English translation (7 pages).

* cited by examiner

NEMATIC LIQUID CRYSTAL COMPOSITION, AND LIQUID CRYSTAL DISPLAY ELEMENT MANUFACTURED USING SAME

TECHNICAL FIELD

The present invention relates to a nematic liquid crystal composition exhibiting a negative dielectric anisotropy ($\Delta\varepsilon$), which is useful as a liquid crystal display material, and a liquid crystal display element using the same.

BACKGROUND ART

Liquid crystal display elements are used for various household electric appliances, measuring instruments, automobile panels, word processors, electronic notebooks, printers, computers, televisions and the like, including timepieces, and calculators. Typical examples of liquid crystal display systems include twisted nematic (TN) type systems, super twisted nematic (STN) type systems, dynamic light scattering (DS) type systems, guest and host (GH) type systems, in-plane switching (IPS) type systems, optically compensated birefringence (OCB) type systems, voltage control birefringence (ECB) type systems, vertically aligned (VA) type systems, color super homeotropic (CSH) type systems, ferroelectric liquid crystal (FLC), and the like. In addition, examples of driving methods include static driving, multiplex driving, a simple matrix method, an active matrix (AM) method driven by a thin film transistor (TFT), a thin film diode (TFD), or the like.

In these display systems, the IPS type systems, the ECB type systems, the VA type systems, the CSH type systems, and the like have a feature of using a liquid crystal material having a negative $\Delta\varepsilon$ value. Among these, in particular, the VA type display method using AM driving is used for display elements which are required to have a high speed and a wide viewing angle, for example, applications such as televisions. A nematic liquid crystal composition used for a display method such as a VA type method requires a high-speed response to correspond to a 3D or high definition display. That is, it is important that the rotational viscosity ($\gamma_1$) of the liquid crystal composition is small, the elastic constant ($K_{33}$) is large, and the value of $\gamma_1/K_{33}$ obtained therefrom is sufficiently small. In addition, from the setting of $\Delta n \times d$ which is the product of the refractive index anisotropy ($\Delta n$) and the cell gap (d), it is necessary to adjust $\Delta n$ of the liquid crystal material within an appropriately large range in accordance with a small cell gap for improving the response speed. In addition, it is required to keep $\gamma_1$ of the liquid crystal composition small.

Until now, the characteristics of the liquid crystal compositions have been improved by researching various compounds having a negative $\Delta\varepsilon$ which has a large absolute value.

A liquid crystal composition using liquid crystal compounds (A) and (B) having a 2,3-difluorophenylene skeleton as described below has been disclosed as a liquid crystal material having a negative $\Delta\varepsilon$ (refer to PTL 1), but without obtaining a sufficiently small $\gamma_1/K_{33}$.

[Chem. 1]

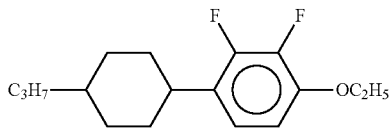
(A)

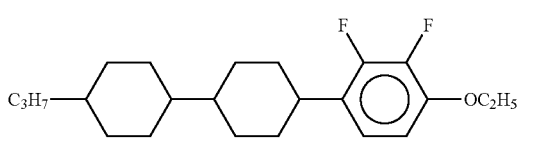
(B)

In addition, although it is possible to reduce the value of $\gamma_1/K_{33}$ by using the liquid crystal compound (N2) and the compound represented by General Formula (N3) as a combination of compounds having $\Delta\varepsilon$ of almost zero (refer to PTL 2), there is a demand for further improvements in response speed.

[Chem. 2]

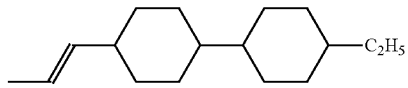
(N2)

[Chem. 3]

(N3)

(in the formula, $R^p$ and $R^q$ each independently represent an alkyl group having 1 to 10 carbon atoms, and ring J, ring F, and ring K each independently represent a trans-1,4-cyclohexylene group or a 1,4-phenylene group).

In addition, PTL 3 discloses that the response speed of a homeotropic liquid crystal cell is improved by using a liquid crystal material having a large index represented by Equation 1, but this is not sufficient.

[Math. 1]

$$FoM = K_{33} \cdot \Delta n^2 / \gamma_1 \qquad \text{(Equation 1)}$$

$K_{33}$: elastic constant
$\Delta n$: refractive index anisotropy
$\gamma_1$: rotational viscosity From the above, in the liquid crystal composition used for a liquid crystal television requiring a high-speed response, it is important that the nematic phase-isotropic liquid phase transition temperature ($T_{NI}$) is high, the refractive index anisotropy ($\Delta n$) is large, the rotational viscosity ($\gamma_1$) is small, the elastic constant ($K_{33}$) is large, and the voltage holding ratio (VHR) is high, in addition, there is a demand for a liquid crystal display element which, when using this liquid crystal composition, has a response speed with excellent display quality and in which there are no defects such as drop marks, burn in, display unevenness, and the like.

CITATION LIST

Patent Literature

[PTL 1] JP-A-8-104869
[PTL 2] JP-A-2013-208201
[PTL 3] JP-A-2006-301643

SUMMARY OF INVENTION

Technical Problem

The problem to be solved by the present invention is to provide a liquid crystal composition in which the nematic phase-isotropic liquid phase transition temperature ($T_{NI}$) is high, the refractive index anisotropy ($\Delta n$) is large, the rotational viscosity ($\gamma_1$) is small, the elastic constant ($K_{33}$) is large, and the voltage holding ratio (VHR) is high, and which has negative dielectric anisotropy ($\Delta\varepsilon$), and furthermore to provide a liquid crystal display element which, when using this liquid crystal composition, has a high response speed with excellent display quality and in which display defects such as drop marks, burn in, display unevenness, and the like are absent or suppressed.

Solution to Problem

The present inventors found that it is possible to solve the above problems with a liquid crystal composition containing a liquid crystal compound having a specific structure, thereby completing the present invention. That is, the liquid crystal composition of the present invention provides a liquid crystal composition having negative dielectric anisotropy which contains one or two or more of compounds represented by General Formula (i):

[Chem. 4]

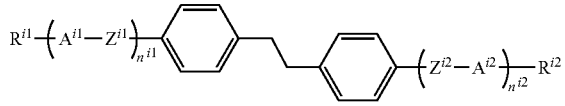

(i)

(in the formula, $R^{i1}$ and $R^{i2}$ each independently represent an alkyl group having 1 to 10 carbon atoms, and one or two or more non-adjacent —CH$_2$— in $R^{i1}$ and $R^{i2}$ may each independently be substituted with —CH=CH—, —C≡C—, —O—, —S—, —COO—, —OCO—, or —CO—, in addition, and one or two or more of the hydrogen atoms present in $R^{i1}$ and $R^{i2}$ may each independently be substituted with a fluorine atom or a chlorine atom;

$A^{i1}$ and $A^{i2}$ each independently represent a groups selected from a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group;

$Z^{i1}$ and $Z^{i2}$ are each independently a single bond, —CH$_2$CH$_2$—, —(CH$_2$)$_4$—, —OCH$_2$—, —CH$_2$O—, —COO—, —OCO—, —OCF$_2$—, —CF$_2$O—, —CH=N—N=CH—, —CH=CH—, —CF=CF—, or —C≡C—;

$n^{i1}$ and $n^{i2}$ each independently represent 0, 1, or 2, provided that $n^{i1}+n^{i2}$ is 1 or more; and in a case where $n^{i1}$ is 2, plural $A^{i1}$'s may be the same or different and plural $Z^{i1}$'s may be the same or different, and in a case where $n^{i2}$ is 2, plural $A^{i2}$'s may be the same or different and plural $Z^{i2}$'s may be the same or different), and also provides a liquid crystal display element using the liquid crystal composition.

Advantageous Effects of Invention

The liquid crystal composition of the present invention has a large refractive index anisotropy ($\Delta n$), a low rotational viscosity ($\gamma_1$), a large elastic constant ($K_{33}$), a high voltage holding ratio (VHR), and a negative dielectric anisotropy ($\Delta\varepsilon$) and the liquid crystal display element using the liquid crystal composition has a high response speed with excellent display quality in which display defects such as drop marks, burn-in, and display unevenness are absent or suppressed.

DESCRIPTION OF EMBODIMENTS

The liquid crystal composition of the present invention contains one or two or more of compounds represented by General Formula (i).

[Chem. 5]

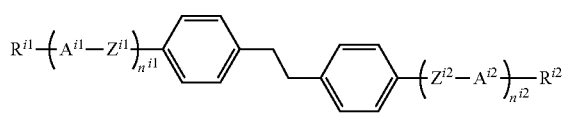

(i)

In General Formula (i), in order to decrease the viscosity, $R^{i1}$ is preferably an alkyl group having 1 to 8 carbon atoms or an alkenyl group having 2 to 8 carbon atoms, more preferably an alkyl group having 1 to 5 carbon atoms or an alkenyl group having 2 to 5 carbon atoms, even more preferably an alkyl group having 1 to 4 carbon atoms or an alkenyl group having 2 to 4 carbon atoms, yet more preferably an alkyl group having 1 to 3 carbon atoms, still more preferably an alkyl group having 1 to 2 carbon atoms, and particularly preferably a methyl group having 1 carbon atom. In order to decrease the viscosity, $R^{i2}$ is preferably an alkyl group having 1 to 8 carbon atoms, more preferably an alkyl group having 1 to 5 carbon atoms, even more preferably an alkyl group having 1 to 4 carbon atoms, yet more preferably an alkyl group having 1 to 3 carbon atoms, still more preferably an alkyl group having 1 to 2 carbon atoms, and particularly preferably a methyl group having 1 carbon atom. In addition, $R^{i1}$ and $R^{i2}$ are preferably linear. More specifically, in order to reduce the value of $\gamma_1/K_{33}$, at least one of $R^{i1}$ and $R^{i2}$ is preferably a methyl group, $R^{i2}$ more preferably represents a methyl group, and $R^{i1}$ and $R^{i2}$ are particularly preferably both methyl groups. In addition, in order to increase the miscibility with other liquid crystal components, $R^{i1}$ and $R^{i2}$ are preferably different.

$A^{i1}$ and $A^{i2}$ are each independently preferably a trans-1,4-cyclohexylene group, a 1,4-phenylene group, a 2-fluoro-1,4-phenylene group, or a 3-fluoro-1,4-phenylene group. In order to decrease the viscosity, $A^{i1}$ and $A^{i2}$ are each independently preferably a trans-1,4-cyclohexylene group, an unsubstituted 1,4-phenylene group, a 2-fluoro-1,4-phenylene group, or a 3-fluoro-1,4-phenylene group, and more preferably a trans-1,4-cyclohexylene group. In order to improve the miscibility with other liquid crystal components, a trans-1,4-cyclohexylene group, a 2-fluoro-1,4-phenylene group, or a 3-fluoro-1,4-phenylene group are preferable. In order to raise the $T_{NI}$, an unsubstituted 1,4-phenylene group or an unsubstituted naphthalene-2,6-diyl group are preferable. In order to improve the long-term reliability of the liquid crystal display element, a nitrogen atom is preferably not contained. From the viewpoint of improving the viscosity, miscibility with other liquid crystal components, and $T_{NI}$ in a well-balanced manner, it is preferable that at least one of $A^{i1}$ or $A^{i2}$ is a trans-1,4-cyclohexylene group and at least one of $A^{i1}$ or $A^{i2}$ is an unsubstituted 1,4-phenylene group, a 2-fluoro-1,4-phenylene group, or a 3-fluoro-1,4-phenylene group. More specifically, in a case where $n^{i1}+n^{i2}$ represents 1, either $A^{i1}$ or $A^{i2}$ is preferably a trans-1,4-cyclohexylene group or an unsubstituted 1,4-phenylene group, a 2-fluoro-1,4-phenylene group, or a 3-fluoro-1,4-phenylene group, and an unsubstituted 1,4-phenylene group is particularly preferable. In a case where $n^{i1}+n^{i2}$ represents 2, either one of $A^{i1}$ or $A^{i2}$ is preferably a trans-1,4-cyclohexylene group and either one of $A^{i1}$ or $A^{i2}$ is preferably an unsubstituted 1,4-phenylene group, a 2-fluoro-1,4-phenylene group, or a 3-fluoro-1,4-phenylene group, $A^{i1}$ is a more preferably a trans-1,4-cyclohexylene group, and $A^{i2}$ is more preferably an unsubstituted 1,4-phenylene group, a 2-fluoro-1,4-phenylene group, or a 3-fluoro-1,4-phenylene group. In addition, in a case where $n^{i1}+n^{i2}$ represents 3, at least, one of $A^{i1}$ or $A^{i2}$ is preferably a trans-1,4-cyclohexylene group, and at least one of $A^{i1}$ or $A^{i2}$ is preferably a 2-fluoro-1,4-phenylene group, or a 3-fluoro-1,4-phenylene group.

$Z^{i1}$ and $Z^{i2}$ are each independently preferably a single bond, —OCH$_2$—, —CH$_2$O—, —CF$_2$O—, —OCF$_2$—, —CH$_2$CH$_2$—, or —CF$_2$CF$_2$—, and more preferably a single bond, —CH$_2$O—, —CF$_2$O—, —CH$_2$CH$_2$—, or —CF$_2$CF$_2$, even more preferably a single bond, —CH$_2$O—, or —CH$_2$CH$_2$—, and particularly preferably a single bond.

$n^{i1}$ and $n^{i2}$ are each independently preferably 0 or 1 when emphasizing viscosity, and 1 or 2 is preferable when emphasizing $T_{NI}$. In order to increase the miscibility with other liquid crystal components, 0 or 1 is preferable. More specifically, $n^{i1}$ is preferably 1 or 2, and $n^{i2}$ is preferably 0.

In a case of emphasizing viscosity, $n^{i1}+n^{i2}$ is preferably 1 or 2, in a case of emphasizing $T_{NI}$, $n^{i1}+n^{i2}$ is preferably 3 or 4, more preferably 3, and 1 or 2 is preferable in order to increase miscibility with other liquid crystal components. From the viewpoint of improving the viscosity, $T_{NI}$, and miscibility with other liquid crystal components in a well-balanced manner, $n^{i1}+n^{i2}$ is preferably 1 or 2, and in a case of emphasizing making the viscosity smaller, $n^{i1}+n^{i2}$ is preferably 1, in a case of emphasizing further increasing the $T_{NI}$ or Δn, $n^{i1}+n^{i2}$ is preferably 1. In a case where $n^{i1}+n^{i2}$ is 2, it is preferable that $n^{i1}$ is 2 and $n^{i2}$ is 0. In a case where $n^{i1}+n^{i2}$ is 3, it is preferable that $n^{i1}$ is 2 and $n^{i2}$ is 1 or $n^{i1}$ is 1 and $n^{i2}$ is 2. In a case where $n^{i1}+n^{i2}$ is 4, it is preferable that $n^{i1}$ is 2 and $n^{i2}$ is 2, or $n^{i1}$ is 3 and $n^{i2}$ is 1, or $n^{i1}$ is 1 and $n^{i2}$ is 3.

Specific examples of preferable compounds are shown below, but the present invention is not limited thereto.

In General Formula (i), each compound represented by General Formulas (ia) to (id) is preferable.

[Chem. 6]

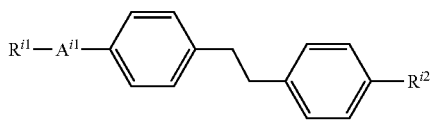
(ia)

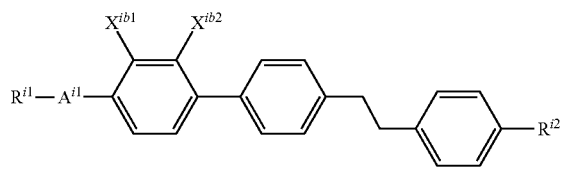
(ib)

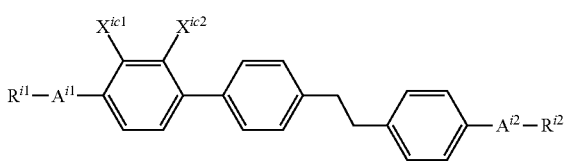
(ic)

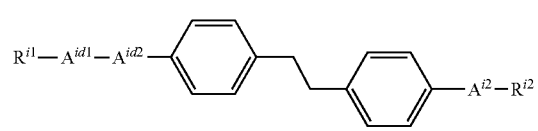
(id)

(In the formulas, $R^{i1}$, $R^{i2}$, $A^{i1}$ and $A^{i2}$ represent the same meanings as $R^{i1}$, $R^{i2}$, $A^{i1}$ and $A^{i2}$ in General Formula (i), respectively, $A^{id1}$ and $A^{id2}$ each independently represent the same meanings as $A^{i1}$ in General Formula (i), $X^{ib1}$, $X^{ib2}$, $X^{ic1}$, and $X^{ic2}$ each independently represent a hydrogen atom or a fluorine atom, provided that $X^{ib1}$ and $X^{ib2}$ do not represent a fluorine atom at the same time and $X^{ic1}$ and $X^{ic2}$ do not represent a fluorine atom at the same time.)

As General Formula (ia), compounds represented by General Formula (ia-1) and General Formula (ia-2) are preferable.

[Chem. 7]

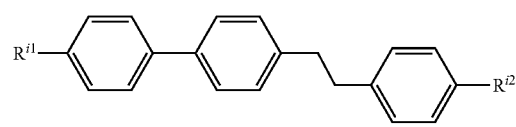
(ia-1)

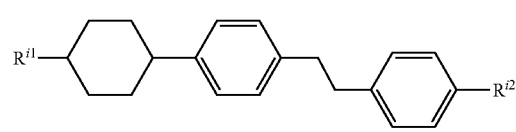
(ia-2)

(In the formulas, $R^{i1}$ and $R^{i2}$ represent the same meanings as $R^{i1}$ and $R^{i2}$ in General Formula (i), respectively.)

In particular, General Formula (ia-1) is preferable.

As General Formula (ib), the compounds represented by General Formula (ib-1) to General Formula (ib-3) are preferable.

[Chem. 8]

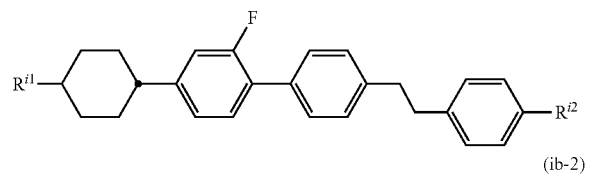
(ib-1)

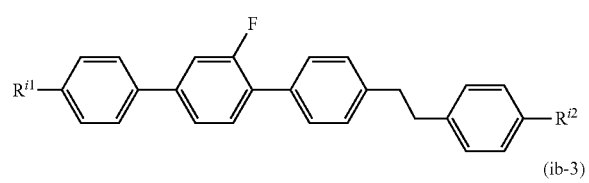
(ib-2)

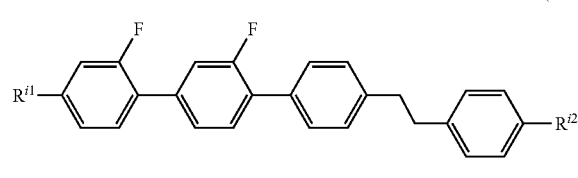
(ib-3)

(In the formulas, $R^{i1}$ and $R^{i2}$ represent the same meanings as $R^{i1}$ and $R^{i2}$ in General Formula (i), respectively.)

In particular, General Formula (ib-1) and General Formula (ib-2) are preferable.

As General Formula (ic), compounds represented by General Formula (ic-1) to General Formula (ic-3) are preferable.

[Chem. 9]

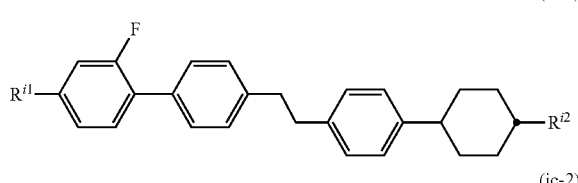
(ic-1)

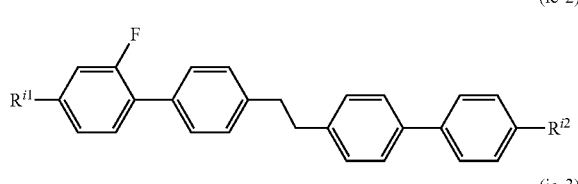
(ic-2)

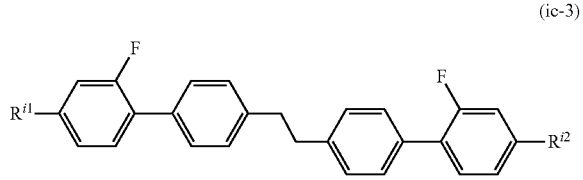
(ic-3)

(In the formula, $R^{i1}$ and $R^{i2}$ represent the same meanings as $R^{i1}$ and $R^{i2}$ in General Formula (i), respectively.)

As General Formula (id), compounds represented by General Formula (id-1) to General Formula (id-4) are preferable.

[Chem. 10]

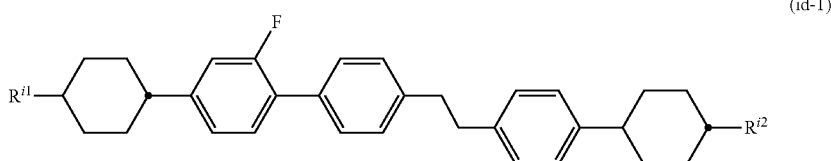
(id-1)

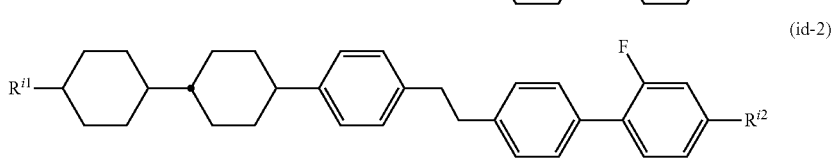
(id-2)

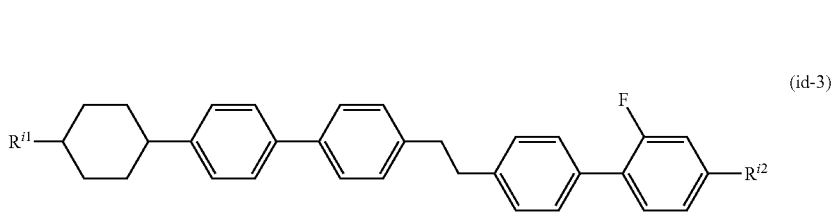
(id-3)

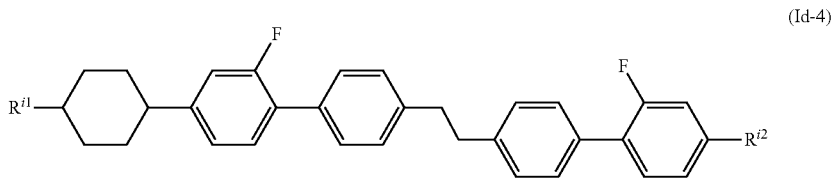
(Id-4)

(In the formulas, $R^{i1}$ and $R^{i2}$ represent the same meanings as $R^{i1}$ and $R^{i2}$ in General Formula (i), respectively.)

In particular, General Formulas (id-1), (id-2), and (id-4) are preferable.

When the content of the compound represented by General Formula (i) in the liquid crystal composition of the present invention is small, the effects thereof do not appear, thus the lower limit value in the composition is preferably 1% by mass (hereinafter, % in the composition represents % by mass) or more, more preferably 2% or more, still more preferably 3% or more, still more preferably 5% or more, still more preferably 8% or more, and still more preferably 10% or more. On the other hand, when the content is large, problems such as precipitation are caused, thus the upper limit value is preferably 70% or less, more preferably 60% or less, preferably 50% or less, preferably 40% or less, preferably 35% or less, preferably 30% or less, preferably 28% or less, preferably 25% or less, preferably 23% or less, preferably 20% or less, preferably 18% or less, preferably 15% or less, and preferably 13% or less. It is also possible to use the compound represented by General Formula (i) as one or two or more of compounds may be used at the same time.

In a case where two or more types of compounds represented by General Formula (i) are used at the same time, it is preferable to select these from compounds represented by General Formula (ib-1) and/or General Formula (ib-2).

Here, the compound represented by General Formula (i) does not have a structure in which the hetero atoms are directly bonded to each other.

The liquid crystal composition of the present invention preferably contains one or two or more of compounds selected from the compounds represented by General Formulas (N-1), (N-2), and (N-3):

[Chem. 11]

(N-1)

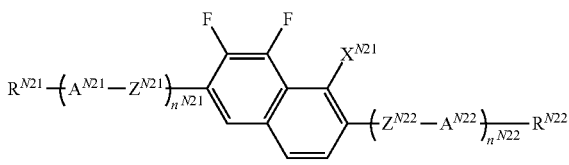
(N-2)

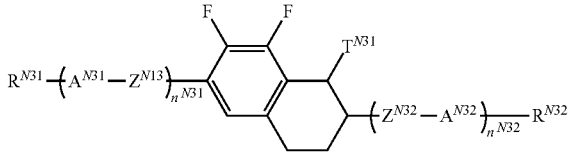
(N-3)

(in the formulas, $R^{N11}$, $R^{N12}$, $R^{N21}$, $R^{N22}$, $R^{N31}$, and $R^{N32}$ each independently represent an alkyl group having 1 to 10 carbon atoms, and one or two or more non-adjacent —$CH_2$— in the alkyl group may each independently be substituted with —CH=CH—, —C≡C—, —O—, —S—, —CO—, —COO—, or —OCO—;

$A^{N11}$, $A^{N12}$, $A^{N21}$, $A^{N22}$, $A^{N31}$, and $A^{N32}$ each independently represent a group selected from the group consisting of (a) a 1,4-cyclohexylene group (one —$CH_2$— or two or more non-adjacent —$CH_2$— present in this group may be substituted with —O—), (b) a 1,4-phenylene group (one —CH= or two or more non-adjacent —CH= present in this group may be substituted with —N=), (c) a naphthalene-2,6-diyl group, a 1,2,3,4-tetrahydronaphthalene-2,6-diyl group, or a decahydronaphthalene-2,6-diyl group (one —CH= or two or more non-adjacent —CH= present in the naphthalene-2,6-diyl group or the 1,2,3,4-tetrahydronaphthalene-2,6-diyl group may be substituted with —N=), and the group (a), the group (b), and the group (c) may each independently be substituted with a cyano group, a fluorine atom, or a chlorine atom;

$Z^{N11}$, $Z^{N12}$, $Z^{N21}$, $Z^{N22}$, $Z^{N31}$, and $Z^{N32}$ each independently represent a single bond, —$CH_2CH_2$—, —$(CH_2)_4$—, —$OCH_2$—, —$CH_2O$—, —COO—, —OCO—, —$OCF_2$—, —$CF_2O$—, —CH=N—N=CH—, —CH=CH—, —CF=CF—, or —C≡C—;

$X^{N21}$ represents a hydrogen atom or a fluorine atom, $T^{N31}$ represents —$CH_2$— or an oxygen atom;

$n^{N11}$, $n^{N12}$, $n^{N21}$, $n^{N22}$, $n^{N31}$ and $n^{N32}$ each independently represent 0, 1, 2, or 3, provided that $n^{N11}+n^{N12}$, $n^{N21}+n^{N22}$ and $n^{N31}+n^{N32}$ are each independently 1, 2, or 3; and in a case where $n^{N11}$ and/or $n^{N12}$ is 2 or 3 and a plurality with respect to each of $A^{N11}$, $A^{N12}$, $Z^{N11}$, and $Z^{N12}$ is present, the groups or bonds may be the same or different, and in a case where $n^{N21}$ and/or $n^{N22}$ is 2 or 3 and a plurality with respect to each of $A^{N21}$, $A^{N22}$, $Z^{N21}$, and $Z^{N22}$ is present, the groups or bonds may be the same or different, and in a case where $n^{N31}$ and/or $n^{N32}$ is 2 or 3 and a plurality with respect to each of $A^{N31}$, $A^{N32}$, $Z^{N31}$, and $Z^{N32}$ is present, the groups or bonds may be the same or different).

The compound represented by General Formulas (N-1), (N-2), and (N-3) is preferably a compound having a negative Δε which has an absolute value of larger than 3.

In General Formulas (N-1), (N-2), and (N-3), $R^{N11}$, $R^{N12}$, $R^{N21}$, $R^{N22}$, $R^{N31}$, and $R^{N32}$ are each independently preferably an alkyl group having 1 to 8 carbon atoms, an alkoxy group having 1 to 8 carbon atoms, an alkenyl group having 2 to 8 carbon atoms, or an alkenyloxy group having 2 to 8 carbon atoms, more preferably an alkyl group having 1 to 5 carbon atoms, an alkoxy group having 1 to 5 carbon atoms, an alkenyl group having 2 to 5 carbon atoms, or an alkenyloxy group having 2 to 5 carbon atoms, even more preferably an alkyl group having 1 to 5 carbon atoms or an alkenyl group having 2 to 5 carbon atoms, still more preferably an alkyl group having 2 to 5 carbon atoms or an alkenyl group having 2 to 3 carbon atoms, and particularly preferably an alkenyl group having 3 carbon atoms (a propenyl group).

In addition, in a case where the ring structure to which the above is bonded is a phenyl group (aromatic), a linear alkyl group having 1 to 5 carbon atoms, a linear alkoxy group having 1 to 4 carbon atoms, and an alkenyl group having 4 to 5 carbon atoms are preferable, in a case where the ring structure to which the above is bonded is a saturated ring structure such as cyclohexane, pyran, dioxane, or the like, a linear alkyl group having 1 to 5 carbon atoms, a linear alkoxy group having 1 to 4 carbon atoms, and a linear alkenyl group having 2 to 5 carbon atoms are preferable. In order to stabilize the nematic phase, the total of the carbon atoms and the oxygen atoms in a case where present is preferably 5 or less, and the group is preferably linear.

The alkenyl group is preferably selected from the group represented by any one of formulas (R1) to (R5). (The black dot in each formula represents a carbon atom in the ring structure.)

[Chem. 12]

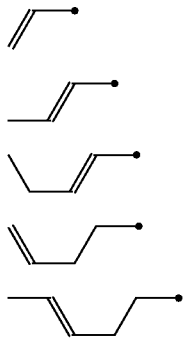

$A^{N11}$, $A^{N12}$, $A^{N21}$, $A^{N22}$, $A^{N31}$, and $A^{N32}$ are each independently preferably aromatic in a case where it is required to increase Δn, preferably aliphatic in order to improve the response speed, and preferably represent a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, more preferably represent any one of the following structures:

[Chem. 13]

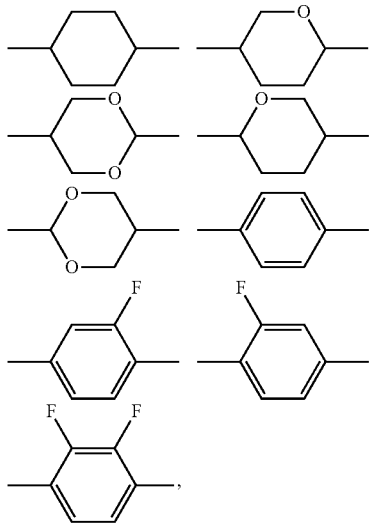

and even more preferably represent a trans-1,4-cyclohexylene group or a 1,4-phenylene group.

$Z^{N11}$, $Z^{N12}$, $Z^{N21}$, $Z^{N22}$, $Z^{N31}$, and $Z^{N32}$ each independently preferably represent —CH$_2$O—, —CF$_2$O—, —CH$_2$CH$_2$—, —CF$_2$CF$_2$—, or a single bond, even more preferably —CH$_2$O—, —CH$_2$CH$_2$—, or a single bond, and particularly preferably —CH$_2$O— or a single bond.

$X^{N21}$ is preferably a fluorine atom.
$T^{N31}$ is preferably an oxygen atom.
$n^{N11}+n^{N12}$, $n^{N21}+n^{N22}$ and $n^{N31}+n^{N32}$ are preferably 1 or 2, and a combination in which $n^{N11}$ is 1 and $n^{N12}$ is 0, a combination in which $n^{N11}$ is 2 and $n^{N12}$ is 0, a combination in which $n^{N11}$ is 1 and $n^{N12}$ is 1, a combination in which $n^{N11}$ is 2 and $n^{N12}$ is 1, a combination in which $n^{N21}$ is 1 and $n^{N22}$ is 0, a combination in which $n^{N21}$ is 2 and $n^{N22}$ is 0, a combination in which $n^{N31}$ is 1 and $n^{N32}$ is 0, a combination in which $n^{N31}$ is 2 and $n^{N32}$ is 0, are preferable.

The lower limit value of the preferable content of the compound represented by Formula (N-1) with respect to the total amount of the composition of the present invention is 1%, 10%, 20%, 30%, 40%, 50%, 55%, 60%, 65%, 70%, 75%, or 80%. The upper limit value of the preferable content is 95%, 85%, 75%, 65%, 55%, 45%, 35%, 25%, or 20%.

The lower limit value of the preferable content of the compound represented by Formula (N-2) with respect to the total amount of the composition of the present invention is 1%, 10%, 20%, 30%, 40%, 50%, 55%, 60%, 65%, 70%, 75%, or 80%. The upper limit value of the preferable content is 95%, 85%, 75%, 65%, 55%, 45%, 35%, 25%, or 20%.

The lower limit value of the preferable content of the compound represented by Formula (N-3) with respect to the total amount of the composition of the present invention is 1%, 10%, 20%, 30%, 40%, 50%, 55%, 60%, 65%, 70%, 75%, or 80%. The upper limit value of the preferable content is 95%, 85%, 75%, 65%, 55%, 45%, 35%, 25%, or 20%.

The total content of General Formulas (N-1), (N-2), and (N-3) with respect to the total amount of the composition of the present invention is preferably 10% to 90% by mass, more preferably 20% to 80% by mass, and particularly preferably 30% to 70% by mass.

In a case where the viscosity of the composition of the present invention is maintained to be low and a composition having a fast response speed is required, it is preferable that the lower limit value is low and the upper limit value is low. Furthermore, in a case where the composition of the present invention maintains a high $T_{NI}$ and a composition with good temperature stability is required, it is preferable that the lower limit value is low and the upper limit value is low. In addition, when it is desired to increase the dielectric anisotropy in order to keep the driving voltage low, it is preferable that the above lower limit value is high and the upper limit value is high.

The compound represented by General Formula (N-1) is a compound in which $A^{N11}$ is a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, $Z^{N11}$ is —OCH$_2$—, —CH$_2$O—, —CF$_2$O—, —OCF$_2$—, —CH$_2$CH$_2$—, —CF$_2$CF$_2$— or a single bond, represents 1, 2, or 3, and $n^{N12}$ is 0.

The compound represented by General Formula (N-1) is preferably a compound represented by General Formula (II).

[Chem. 14]

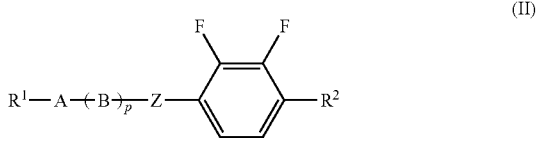

(II)

(In the formula, $R^1$ and $R^2$ each independently represent an alkyl group having 1 to 10 carbon atoms, an alkoxyl group having 1 to 10 carbon atoms, an alkenyl group having 2 to 10 carbon atoms, or an alkenyloxy group having 2 to 10 carbon atoms, one —CH$_2$— or two or more non-adjacent —CH$_2$— present in $R^1$ and $R^2$ may each independently be substituted with —O— and/or —S—. A and B each independently represent a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, and p represents 0, 1 or 2. Z represents —OCH$_2$—, —CH$_2$O—, —CF$_2$O—, —OCF$_2$—, —CH$_2$CH$_2$—, —CF$_2$CF$_2$—, or a single bond.)

$R^1$ and $R^2$ in General Formula (II) are each independently preferably a linear alkyl group having 1 to 5 carbon atoms, an alkoxyl group having 1 to 5 carbon atoms, an alkenyl group having 2 to 5 carbon atoms or an alkenyloxy group having 2 to 5 carbon atoms, $R^1$ is particularly preferably an alkyl group having 1 to 5 carbon atoms or an alkenyl group having 2 to 5 carbon atoms, and $R^2$ is particularly preferably an alkoxyl group having 1 to 5 carbon atoms.

A and B in General Formula (II) are each independently more preferably a trans-1,4-cyclohexylene group, a 1,4-phenylene group, a 2-fluoro-1,4-phenylene group, a 3-fluoro-1,4-phenylene group, a 3,5-difluoro-1,4-phenylene group, or a 2,3-difluoro-1,4-phenylene group, and particularly preferably a trans-1,4-cyclohexylene group or a 1,4-phenylene group.

More preferably, p in the formula is each independently 0 or 1.

Z in the formula is more preferably —CH$_2$O—, —CF$_2$O—, —CH$_2$CH$_2$—, or a single bond, particularly preferably —CH$_2$O— or a single bond.

The liquid crystal composition of the present invention preferably contains one or two or more of compounds represented by General Formula (II), and preferably contains two to ten types of compounds.

The compound represented by General Formula (II) is preferably General Formula (II-A1) to General Formula (II-A5) and General Formula (II-B1) to General Formula (II-B5), more preferably a compound of General Formula (II-A1) to General Formula (II-A5), and particularly preferably a compound of General Formula (II-A1) or General Formula (II-A3).

[Chem. 15]

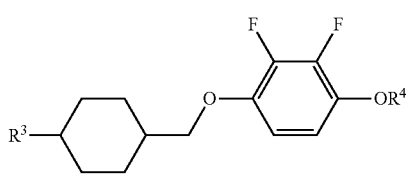
(II-A1)

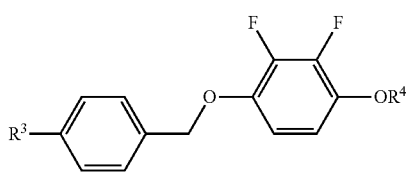
(II-A2)

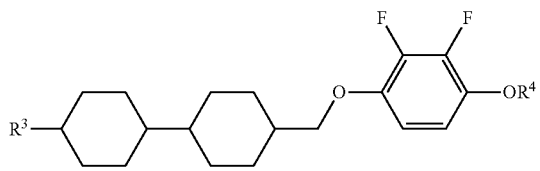
(II-A3)

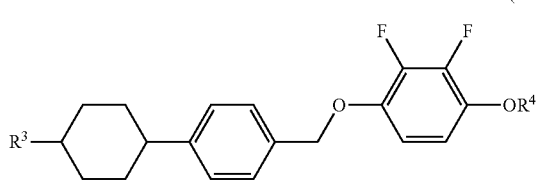
(II-A4)

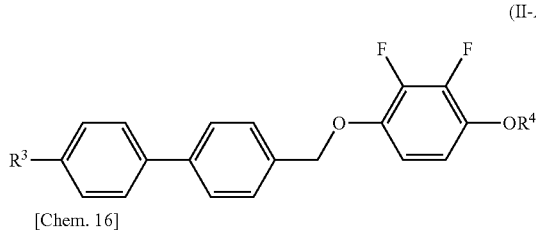
(II-A5)

[Chem. 16]

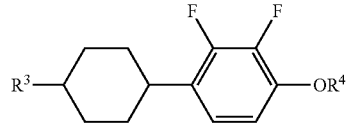
(II-B1)

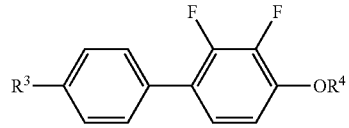
(II-B2)

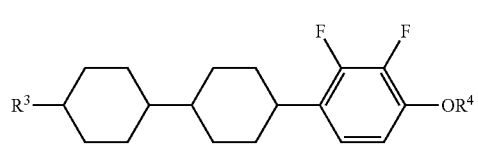
(II-B3)

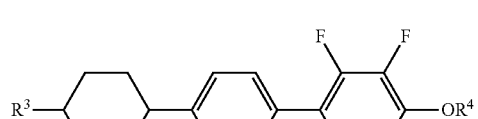
(II-B4)

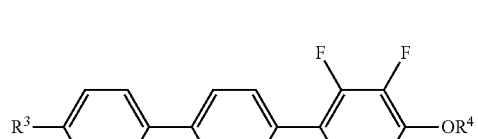
(II-B5)

In the formulas, $R^3$ and $R^4$ each independently represent an alkyl group having 1 to 5 carbon atoms or an alkenyl group having 2 to 5 carbon atoms.

The compound represented by General Formula (II) is preferably a compound represented by General Formulas (II-C1) to (II-C8) below, and more preferably General Formula (II-C1).

[Chem. 17]

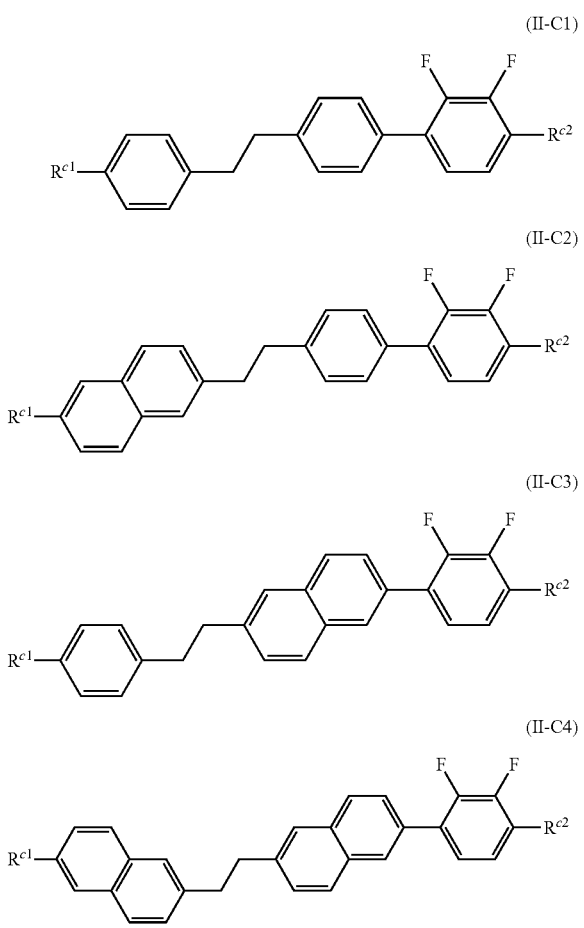

(II-C1)
(II-C2)
(II-C3)
(II-C4)

[Chem. 18]

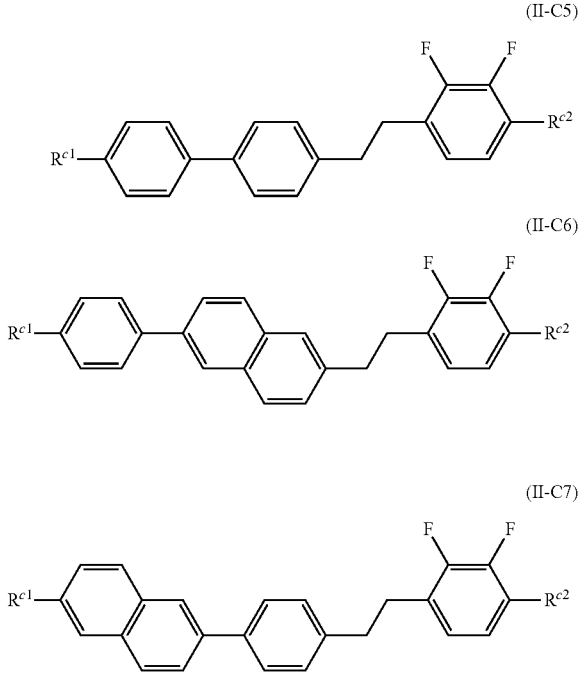

(II-C5)
(II-C6)
(II-C7)

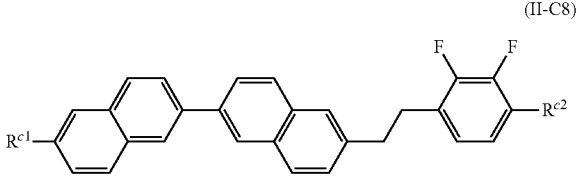

(II-C8)

In the formulas, $R^{c1}$ and $R^{c2}$ each independently represents an alkyl group having 1 to 5 carbon atoms, an alkoxy group having 1 to 5 carbon atoms, an alkenyl group having 2 to 5 carbon atoms, or an alkenyloxy group having 2 to 5 carbon atoms.

In addition, in the compound represented by General Formula (N-1), $A^{N11}$ and $A^{N12}$ are preferably a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, $Z^{N11}$ and $Z^{N12}$ are preferably —OCH$_2$—, —CH$_2$O—, —CF$_2$O—, —OCF$_2$—, —CH$_2$CH$_2$—, —CF$_2$CF$_2$—, or a single bond, and $n^{N11}$ and $n^{N12}$ are preferably 1 or 2.

The compound represented by General Formula (N-1) is preferably a compound represented by General Formula (V).

[Chem. 19]

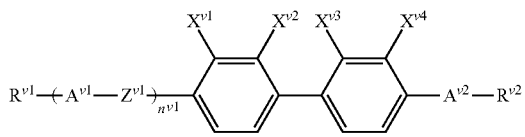

(V)

(In the formula, $R^{v1}$ and $R^{v2}$ each independently represent an alkyl group having 1 to 10 carbon atoms, an alkoxyl group having 1 to 10 carbon atoms, an alkenyl group having 2 to 10 carbon atoms, or an alkenyloxy group having 2 to 10 carbon atoms, one —CH$_2$— or two or more non-adjacent —CH$_2$— present in $R^{v1}$ and $R^{v2}$ may each independently be substituted with —O— and/or —S—. $A^{v1}$ and $A^{v2}$ each independently represent a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group. $n^{v1}$ represents 0, 1, or 2. $Z^{v1}$ represents —OCH$_2$—, —CH$_2$O—, —CF$_2$O—, —OCF$_2$—, —CH$_2$CH$_2$—, —CF$_2$CF$_2$—, or a single bond. $X^{v1}$, $X^{v2}$, $X^{v3}$, and $X^{v4}$ each represent a hydrogen atom or a fluorine atom, but at least one combination of $X^{v1}$ and $X^{v2}$ or $X^{v3}$ and $X^{v4}$ also represents a fluorine atom. However, the compound represented by General Formula (II) is excluded.)

General Formula (V) preferably represents General Formulas (V-1) to (V-10), more preferably represents General Formula (V-1), General Formula (V-3), General Formula (V-4), and General Formula (V-11), and even more preferably represents General Formula (V-1) and General Formula (V-11). It is preferable that the liquid crystal composition of the present invention always contains the compound represented by General Formula (V-1).

[Chem. 20]

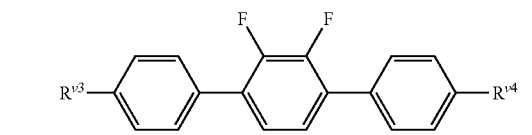
(V-1)

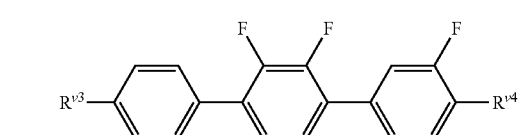
(V-2)

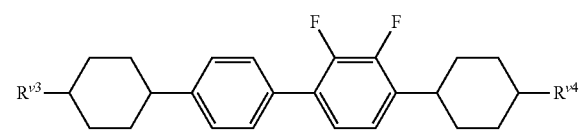
(V-3)

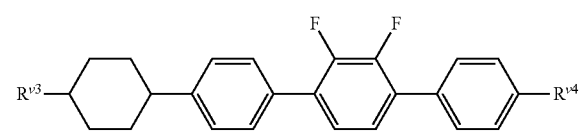
(V-4)

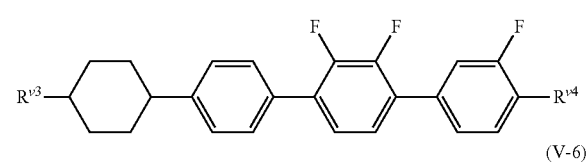
(V-5)

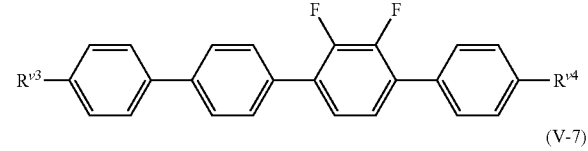
(V-6)

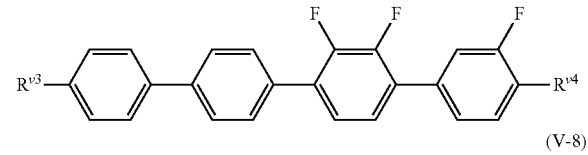
(V-7)

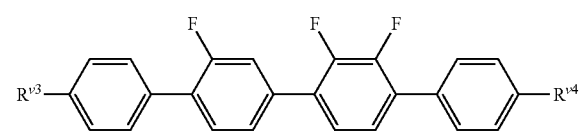
(V-8)

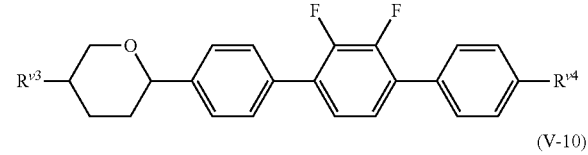
(V-9)

(V-10)

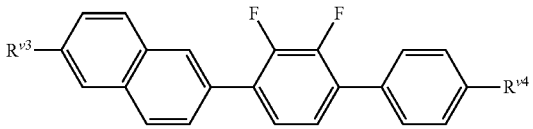
(V-11)

(In the formulas, $R^{v3}$ and $R^{v4}$ each independently represent an alkyl group having 1 to 8 carbon atoms, an alkoxyl group having 1 to 8 carbon atoms, an alkenyl group having 2 to 8 carbon atoms or an alkenyloxy group having 2 to 8 carbon atoms.)

The combination of $R^{v3}$ and $R^{v4}$ is not particularly limited but it is preferable that both represent an alkyl group, both represent an alkenyl group, one represents an alkyl group and the other represents an alkenyl group, one represents an alkyl group and the other represents an alkoxy group, or one represents an alkyl group and the other represents an alkenyloxy group, and it is more preferable that both represent an alkyl group or both represent an alkenyl group.

The liquid crystal composition of the present invention further contains one or two or more of a compound represented by General Formula (L):

[Chem. 21]

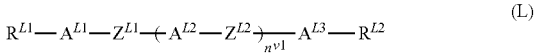
(L)

(in the formula, $R^{L1}$ and $R^{L2}$ each independently represent an alkyl group having 1 to 10 carbon atoms, and one or two or more non-adjacent —CH$_2$— in the alkyl group may each independently be substituted with —CH=CH—, —C≡C—, —O—, —CO—, —COO—, or —OCO—;

$n^{L1}$ represents 0, 1, 2, or 3;

$A^{L1}$, $A^{L2}$, and $A^{L3}$ each independently preferably represent a group selected from the group consisting of:

(a) a 1,4-cyclohexylene group (one —CH$_2$— or two or more non-adjacent —CH$_2$— present in this group may be substituted with —O—), (b) a 1,4-phenylene group (one —CH= or two or more non-adjacent —CH= present, in this group may be substituted with —N=), and (c) a naphthalene-2,6-diyl group, a 1,2,3,4-tetrahydronaphthalene-2,6-diyl group, or a decahydronaphthalene-2,6-diyl group (one —CH= or two or more non-adjacent —CH= present in the naphthalene-2,6-diyl group or the 1,2,3,4-tetrahydronaphthalene-2,6-diyl group may be substituted with —N=), and the group (a), the group (b), and the group (c) may each independently be substituted with a cyano group, a fluorine atom, or a chlorine atom;

$Z^{L1}$ and $Z^{L2}$ each independently represent a single bond, —CH$_2$CH$_2$—, —(CH$_2$)$_4$—, —OCH$_2$—, —CH$_2$O—, —COO—, —OCO—, —OCF$_2$—, —CF$_2$O—, —CH=N—N=CH—, —CH=CH—, —CF=CF—, or —O≡C—; and in a case where $n^{L1}$ is 2 or 3 and plural $A^{L2}$'s are present, these may be the same or different, and in a case where $n^{L1}$ is 2 or 3 and plural $Z^{L2}$'s are present, these may be the same or different, provided that compounds represented by General Formula (i) and the compounds represented by General Formula (N-1), General Formula (N-2), and General Formula (N-3) are excluded).

The compounds represented by General Formula (L) may be used singly, but use in combination is also possible. There is no particular limitation on the type of compounds which are able to be combined, but the compounds are used by being combined appropriately according to desired performances such as solubility at low temperature, transition temperature, electrical reliability, birefringence, and the like. Regarding the types of the compound to be used, for example, one embodiment of the present invention uses one type of compound. In other embodiments of the present invention, two types, three types, four types, five types, six types, seven types, eight, types, nine types, and ten or more types of compounds may be used.

In the composition of the present, invention, it is necessary to appropriately adjust the content of the compound represented by General Formula (L) according to required performances such as the solubility at a low temperature, the transition temperature, the electrical reliability, the birefringence, the process adaptability, the drop marks, the burn-in, and the dielectric anisotropy.

The lower limit value of the preferable content of the compound represented by Formula (L) with respect to the total amount of the composition of the present invention is 1%, 10%, 20%, 30%, 40%, 50%, 55%, 60%, 65%, 70%, 75%, or 80%. The upper limit value of the preferable content is 95%, 85%, 75%, 65%, 55%, 45%, 35%, or 25%.

In a case where the composition of the present invention is maintained at a low viscosity and a composition having a fast response speed is required, it is preferable that the lower limit value is high and the upper limit value is high. Furthermore, in the case where a composition with good temperature stability is required while maintaining the $T_{NI}$ of the composition of the present invention to be high, it is preferable that the lower limit value is high and the upper limit value is high. In addition, when if is desired to increase the dielectric anisotropy in order to keep the driving voltage low, it is preferable that the lower limit value is low and the upper limit value is low.

In a case of emphasizing reliability, it is preferable that both $R^{L1}$ and $R^{L2}$ are alkyl groups, in a case of emphasizing reducing the volatility of the compound, an alkoxy group is preferable, and in a case of emphasizing reduction in viscosity, at least one is preferably an alkenyl group.

In a case where the ring structure to which $R^{L1}$ and $R^{L2}$ are bonded is a phenyl group (aromatic), a linear alkyl group having 1 to 5 carbon atoms, a linear alkoxy group having 1 to 4 carbon atoms, and an alkenyl group having 4 to 5 carbon atoms are preferable, and in a case where the ring structure to which $R^{L1}$ and $R^{L2}$ are bonded is a saturated ring structure such as cyclohexane, pyran, or dioxane, a linear alkyl group having 1 to 5 carbon atoms, a linear alkoxy group having 1 to 4 carbon atoms and a linear alkenyl group having 2 to 5 carbon atoms are preferable. In order to stabilize the nematic phase, the total of the carbon atoms and the oxygen atoms when present is preferably 5 or less, and the group is preferably linear.

The alkenyl group is preferably selected from a group represented by any one of Formula (R1) to Formula (R5). (The black dot in each formula represents a carbon atom in the ring structure.)

[Chem. 22]

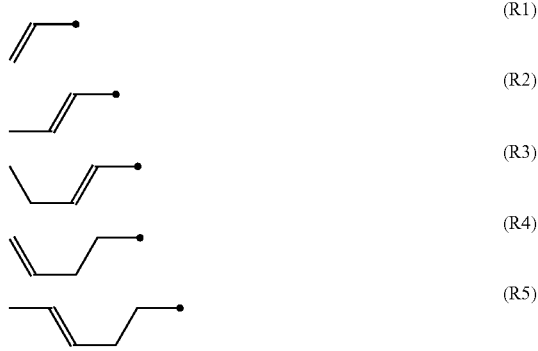

$n^{L1}$ is preferably 0 in a case of emphasizing the response speed, 2 or 3 is preferable for improving the upper limit temperature of the nematic phase, and 1 is preferable for balancing these. In addition, in order to satisfy the properties required for the composition, it is preferable to combine compounds with different values.

$A^{L1}$, $A^{L2}$, and $A^{L3}$ are preferably aromatic in a case where it is required to increase Δn, preferably aliphatic in order to improve the response speed, each independently preferably represents a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, more preferably represents any one of the following structures:

[Chem. 23]

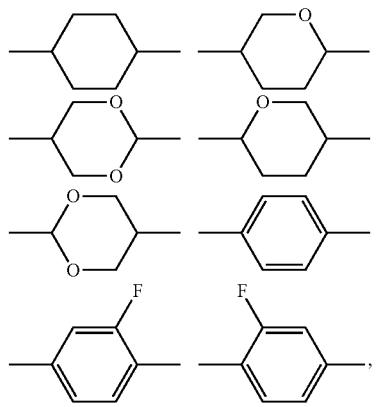

and more preferably a trans-1,4-cyclohexylene group or a 1,4-phenylene group.

$Z^{L1}$ and $Z^{L2}$ are preferably single bonds in a case of emphasizing the response speed.

As the compound represented by General Formula (L), one or two or more of compounds selected from the group of compounds represented by General Formula (III-A) to General Formula (III-K) are contained, and the content thereof is preferably 1% by mass to 60% by mass, preferably 10% by mass to 50% by mass, preferably 20% by mass to 50% by mass, and preferably 20% by mass to 40% by mass based on the total amount of the liquid crystal composition.

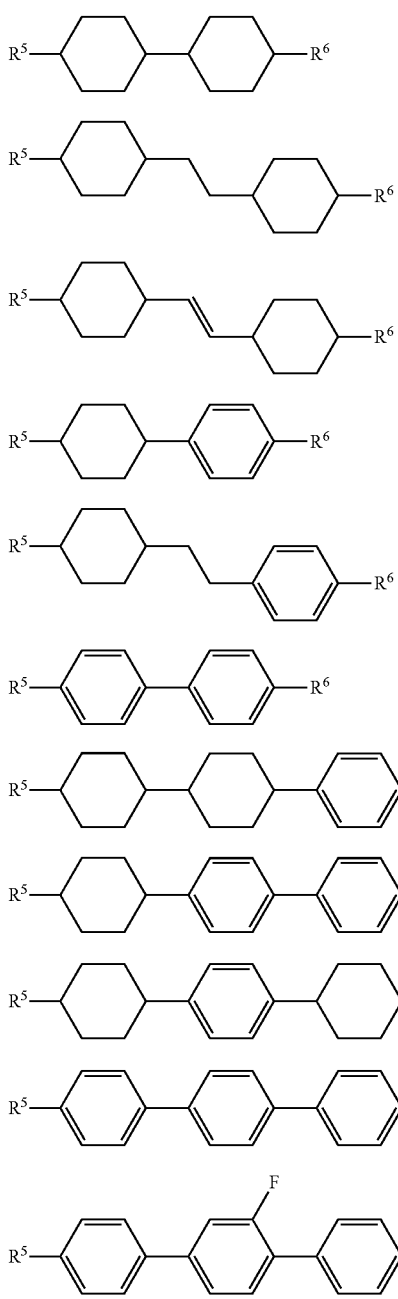

General Formula (III-G), and General Formula (III-H), even more preferably a compound selected from General Formula (III-A), General Formula (III-G), and General Formula (III-H), and also preferably a compound selected from General Formula (III-A), General Formula (III-F), and General Formula (III-H). More specifically, in a case where a large Δn is required, a compound selected from General Formula (III-F), General Formula (III-H), and General Formula (III-K) is preferable.

In addition, in the compounds represented by General Formula (III-D), General Formula (III-G), and General Formula (III-H), $R^5$ is preferably an alkyl group having 1 to 5 carbon atoms or an alkenyl group having 2 to 5 carbon atoms and $R^6$ is preferably an alkyl group having 1 to 5 carbon atoms or an alkoxy group having 1 to 5 carbon atoms, $R^5$ is more preferably an alkenyl group having 2 to 5 carbon atoms and even more preferably an alkenyl group having 2 or 3 carbon atoms, and, in the compound represented by General Formula (III-F), $R^5$ and $R^6$ are each independently preferably an alkyl group having 1 to 5 carbon atoms or an alkenyl group having 2 to 5 carbon atoms.

Preferable specific examples of the compound represented by General Formula (L) include the following.

[Chem. 25]

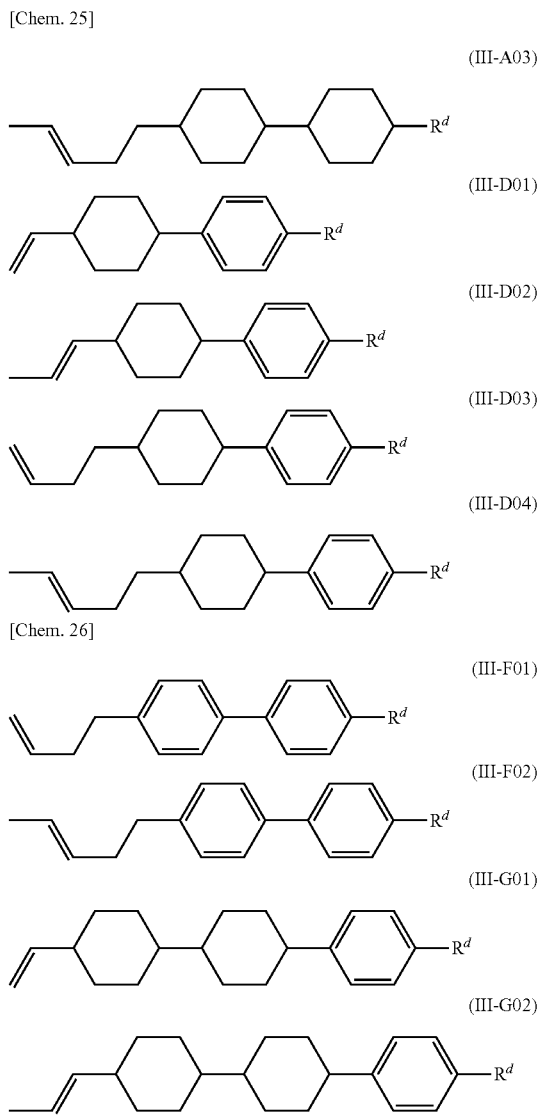

(In the formulas, $R^5$ represents an alkyl group having 1 to 5 carbon atoms or an alkenyl group having 2 to 5 carbon atoms, and $R^6$ represents an alkyl group having 1 to 5 carbon atoms, an alkoxyl group having 1 to 5 carbon atoms, an alkenyl group having 2 to 5 carbon atoms, or an alkenyloxy group having 2 to 5 carbon atoms. However, in the compound represented by General Formula (III-A), the same compound as the compound represented by Formula (I) is not included.)

General Formula (L) is preferably a compound selected from General Formula (III-A), General Formula (III-D), General Formula (III-F), General Formula (III-G), and General Formula (III-H), more preferably a compound selected from General Formula (III-A), General Formula (III-F), -continued

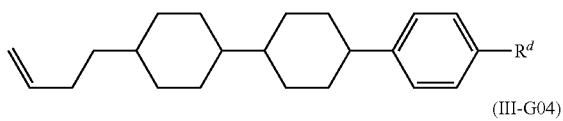
(III-G03)

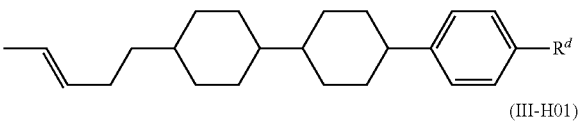
(III-G04)

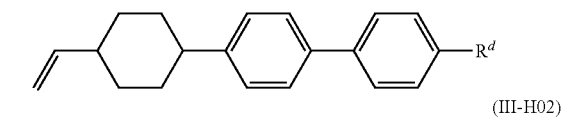
(III-H01)

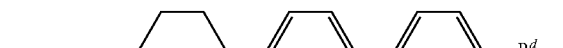
(III-H02)

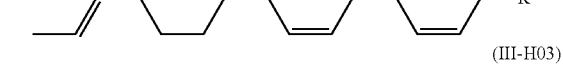
(III-H03)

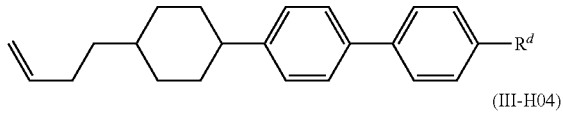
(III-H04)

(In the formulas, $R^d$ represents an alkyl group having 1 to 5 carbon atoms, an alkoxyl group having 1 to 5 carbon atoms, an alkenyl group having 2 to 5 carbon atoms, or an alkenyloxy group having 2 to 5 carbon atoms.)

In addition, as the compound represented by General Formula (L), one or two or more of compounds represented by General Formula (N-001) may be contained.

[Chem. 27]

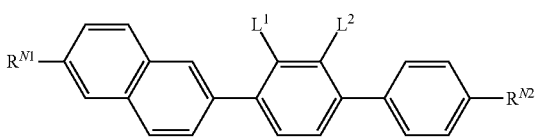
(N-001)

(In the formula, $R^{N1}$ and $R^{N2}$ each independently represent an alkyl group having 1 to 8 carbon atoms, an alkoxyl group having 1 to 8 carbon atoms, an alkenyl group having 2 to 8 carbon atoms, or an alkenyloxy group having 2 to 8 carbon atoms, and $L^1$ and $L^2$ each independently represent a hydrogen atom, a fluorine atom, $CH_3$ or $CF_3$. However, cases where both $L^1$ and $L^2$ represent a fluorine atom are excluded.)

$R^{N1}$ and $R^{N2}$ preferably represent an alkyl group having 1 to 5 carbon atoms.

The liquid crystal composition of the present invention preferably contains the compounds of General Formula (i), General Formula (II-A1), and General Formula (III-A) at the same time, preferably contains the compounds of General Formula (i), General Formula (II-A3), and General Formula (III-A) at the same time, preferably contains the compounds of General Formula (i), General Formula (II-B1), and General Formula (III-A) at the same time, preferably contains the compounds of General Formula (i), General Formula (II-B2), and General Formula (III-A) at the same time, preferably contains the compounds of General Formula (i), General Formula (II-B3), and General Formula (III-A) at the same time, and preferably contains the compounds of General Formula (i), General Formula (II-B4), and General Formula (III-A) at the same time; however, it is even more preferable to contain the compounds of General Formula (i), General Formula (II-A1), and General Formula (III-A) at the same time, even more preferable to contain the compounds of General Formula (i), General Formula (II-A3), and General Formula (III-A) at the same time, and particularly preferable to contain the compounds of General Formula (i), General Formula (II-A1), General Formula (II-A3), and General Formula (III-A) at the same time.

In the liquid crystal composition of the present invention, the total content of the compound represented by General Formula (i), a compound selected from and the compounds represented by General Formula (N-1), General Formula (N-2), and General Formula (N-3), and the compound represented by General Formula (L) is preferably 50 to 100% by mass, more preferably 55 to 100% by mass, even more preferably 60 to 100% by mass, still more preferably 65 to 100% by mass, still more preferably 70 to 100% by mass, and particularly preferably 75 to 100% by mass. More specifically, in the liquid crystal composition of the present invention, the total content of the compounds represented by General Formula (i), General Formula (II), and General Formulas (III-A) to (III-J) is preferably 85 to 100% by mass, and more preferably 90 to 100% by mass, while the total content of the compounds represented by General Formula (i), General Formula (II), General Formula (III-A) to General Formula (III-J) and General Formula (V-1) is even more preferably 30 to 100% by mass, and particularly preferably 95 to 100% by mass.

In the liquid crystal composition of the present invention, the total content of the compounds selected from the compound represented by General Formula (i) and the compounds represented by General Formula (N-1), General Formula (N-2), and General Formula (N-3), is preferably 30% by mass (below, % in the composition represents % by mass) or more as the lower limit value in the composition, preferably 35% or more, preferably 40% or more, preferably 45% or more, preferably 50% or more, preferably 55% or more, preferably 60% or more, preferably 65% or more, preferably 70% or more, preferably 75% or more, preferably 78% or more, preferably 80% or more, preferably 83% or more, preferably 85% or more, preferably 90% or more, and preferably 91% or more. In addition, the upper limit value is preferably 100% or less, preferably 99% or less, preferably 95% or less, preferably 90% or less, preferably 85% or less, preferably 80% or less, preferably 75% or less, preferably 70% or less, preferably 65% or less, preferably 60% or less, preferably 55% or less, and preferably 50% or less.

The composition of the present invention preferably does not contain a compound having a structure in which oxygen atoms are bonded to each other such as a per acid (—CO—OO—) structure in the molecule.

In a case of emphasizing the reliability and long-term stability of the composition, the content of the compound having a carbonyl group is preferably 5% or less with respect to the total mass of the composition, more preferably 3% or less, even more preferably 1% or less, and most preferably substantially not contained.

In a case of emphasizing stability regarding UV irradiation, the content of the compound substituted with chlorine atom with respect to the total mass of the composition is preferably 15% or less, preferably 10% or less, preferably 8% or less, more preferably 5% or less, preferably 3% or less, and even more preferably substantially not contained.

It is preferable to increase the content of the compound in which all the ring structures in the molecule are 6-membered rings, and the content of the compound in which all the ring structures in the molecule are 6-membered rings with respect to the total mass of the composition is preferably 80% or more, more preferably 90% or more, and even more preferably 95% or more, and the composition is most preferably formed only of the compound in which substantially all the ring structures in the molecule are 6-membered rings.

In order to suppress deterioration due to oxidation of the composition, it is preferable to reduce the content of the compound having a cyclohexenylene group as a ring structure, and the content of the compound having a cyclohexenylene group with respect to the total mass of the composition is preferably 10% or less, preferably 8% or less, more preferably 5% or less, more preferably 3% or less, and even more preferably substantially not contained.

In a case of emphasizing improvement of viscosity and improvement of $T_{NI}$, it is preferable to reduce the content of a compound having a 2-methylbenzene-1,4-diyl group in the molecule, the hydrogen atom of which may be substituted with halogen, and the content of the compound having the 2-methylbenzene-1,4-diyl group in the molecule with respect to the total mass of the composition is preferably 10% or less, preferably 8% or less, more preferably 5% or less, more preferably 3% or less, and even more preferably substantially not contained.

In the present application, "substantially not contained" means that the contained substance is not contained except unintentionally.

In a case where the compound contained in the composition of the first embodiment of the present invention has an alkenyl group as a side chain and in a case where the alkenyl group is bonded to cyclohexane, the number of carbon atoms of the alkenyl group is preferably 2 to 5, and in a case where the alkenyl group is bonded to benzene, the number of carbon atoms of the alkenyl group is preferably 4 to 5, and the unsaturated bond of the alkenyl group and benzene are preferably not directly bonded. The liquid crystal composition of the present invention has a dielectric anisotropy ($\Delta\varepsilon$) of $-2.0$ to $-8.0$ at 25° C., preferably $-2.0$ to $-6.0$, more preferably $-2.0$ to $-5.0$, and particularly preferably $-2.5$ to $-4.0$.

The liquid crystal composition of the present invention has a refractive index anisotropy ($\Delta n$) of 0.08 to 0.14 at 25° C., more preferably 0.09 to 0.13, and particularly preferably 0.09 to 0.12. More specifically, in a case of handling a thin cell gap, 0.10 to 0.13 is preferable and, in a case of handling a thick cell gap, 0.08 to 0.10 is preferable.

The liquid crystal composition of the present invention has a viscosity ($\eta$) at 25° C. of 10 to 50 mPa·s, more preferably 10 to 45 mPa·s, and particularly preferably 10 to 40 mPa·s.

The liquid crystal composition of the present invention has a rotational viscosity ($\gamma_1$) at 25° C. of 60 to 200 mPa·s, more preferably 60 to 180 mPa·s, and particularly preferably 70 to 170 mPa·s.

The liquid crystal composition of the present invention has a nematic phase-isotropic liquid phase transition temperature ($T_{NI}$) of 60° C. to 120° C., more preferably 70° C. to 110° C., and particularly preferably 72° C. to 105° C.

The liquid crystal composition of the present invention has an elastic constant ($K_{33}$) of 10.0 to 20.0, more preferably 11.0 to 19.0, and particularly preferably 11.0 to 18.0. In more detail, the lower limit value of the elastic constant ($K_{33}$) is preferably 11.0, preferably 11.5, preferably 12.0, preferably 12.5, preferably 13.0, preferably 13.5, preferably 14.0, preferably 14.5, preferably 15.0, and preferably 15.5.

In addition to the above compounds, the liquid crystal composition of the present invention may contain an ordinary nematic liquid crystal, a smectic liquid crystal, a cholesteric liquid crystal, an antioxidant, an ultraviolet absorber, a polymerizable monomer, a light stabilizer (HALS), or the like.

For example, it is preferable to contain one or two or more polymerizable compounds such as biphenyl derivatives and terphenyl derivatives as polymerizable monomers, and the polymerizable compound is preferably contained in an amount of 0.01% by mass to 2% by mass with respect to the total amount, of the composition of the present invention. More specifically, the liquid crystal composition of the present invention preferably contains one or two or more polymerizable compounds represented by General Formula (VI):

[Chem. 28]

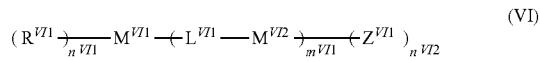

(in the formula, $Z^{VT1}$ represents a hydrogen atom, an alkyl group having 1 to 12 carbon atoms, an alkoxy group having 1 to 12 carbon atoms or $P^{VT2}$—$S^{VT2}$—, $R^{VT1}$ represents $P^{VT1}$—$S^{VT1}$—, $P^{VT1}$ and $P^{VT2}$ each independently represent a group selected from Formula (R-1) to Formula (R-15):

[Chem. 29]

(R-1)

(R-2)

(R-3)

(R-4)

(R-5)

(R-6)

(R-7)

-continued

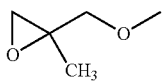
(R-8)

(R-9)

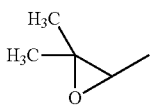
(R-10)

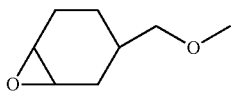
(R-11)

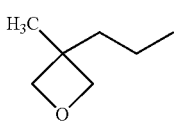
(R-12)

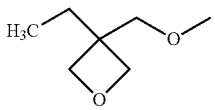
(R-13)

(R-14)

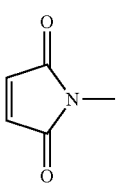

HS— (R-15)

$S^{VT1}$ and $S^{VT2}$ each independently represent a single bond or an alkylene group having 1 to 15 carbon atoms, one —CH$_2$— or two or more non-adjacent —CH$_2$— in the alkylene group may be substituted with —O—, —OCO—, or —COO—, provided that the oxygen atoms are not directly adjacent to each other, $n^{VT1}$ represents an integer of 1 to 3, $n^{VT2}$ represents an integer of 1 to 3, $m^{VT1}$ represents an integer of 0 to 4, $M^{VT1}$ is a divalent cyclic group selected from a 1,4-phenylene group, a 1,4-cyclohexylene group, a pyridine-2,5-diyl group, a pyrimidine-2,5-diyl group, a naphthalene-2,6-diyl group, an indane-2,5-diyl group, a 1,2,3,4-tetrahydronaphthalene-2,6-diyl group, a 1,3-dioxane-2,5-diyl group, or a phenanthrene-2,7-diyl group, in a case where $n^{VT1}$ represents 2 or 3, and/or in a case where $m^{VT1}$ represents 0 and $n^{VT2}$ represents 2 or 3, the compound further has a bond at an arbitrary position of the divalent cyclic group, $M^{VT2}$ each independently represents a divalent cyclic group selected from a 1,4-phenylene group, a 1,4-cyclohexylene group, a pyridine-2,5-diyl group, a pyrimidine-2,5-diyl group, a naphthalene-2,6-diyl group, an indane-2,5-diyl group, a 1,2,3,4-tetrahydronaphthalene-2,6-diyl group, a 1,3-dioxane-2,5-diyl group, or a phenanthrene-2,7-diyl group, in a case where $n^{VT2}$ represents 2 or 3, $M^{VT2}$ to which $Z^{VT1}$ is linked has a further bond at an arbitrary position of the divalent cyclic group ($M^{VT2}$ to which Z is not linked are each independently selected from the divalent cyclic groups), at least one cyclic group of $M^{VT1}$ and $M^{VT2}$ present may be substituted with one or more alkyl groups having 1 to 12 carbon atoms, alkoxy groups having 1 to 12 carbon atoms, or halogens, $L^{VT1}$ is a single bond, —O—, —S—, —CH$_2$—, —OCH$_2$—, —CH$_2$O—, —CO—, —C$_2$H$_4$—, —COO—, —OCO—, —OCOOCH$_2$—, —CH$_2$OCOO—, —OCH$_2$CH$_2$O—, —CO—NR$^a$—, —NR$^a$—CO—, —SCH$_2$—, —CH$_2$S—, —CH=CR$^a$—COO—, —CH=CR$^a$—OCO—, —COO—CR$^a$=CH—, —OCO—CR$^a$=CH—, —COO—CR$^a$=CH—COO—, —COO—CR$^a$=CH—OCO—, —OCO—CR$^a$=CH—COO—, —OCO—CR$^a$=CH—OCO—, —(CH$_2$)$_Y$—C(=O)—O—, —(CH$_2$)$_Y$—O—(C=O), —O—(C=O)—(CH$_2$)$_Y$—, —(C=O)—O—(CH$_2$)$_Y$—, —CH=CH—, —CF=CF—, —CF=CH—, —CH=CF—, —CF$_2$—, —CF$_2$O—, —OCF$_2$—, —CF$_2$CH$_2$—, —CH$_2$CF$_2$—, —CF$_2$CF$_2$—, or —C≡C—, (where each $R^a$ independently represents a hydrogen atom or an alkyl group having 1 to 4 carbon atoms and Y represents an integer of 1 to 4), in a case where a plurality with respect to each of $R^{VT1}$, $Z^{VT1}$, $L^{VT1}$ and $M^{VT2}$, is present, these may be the same or different.)

In the formula, $Z^{VT1}$ preferably represents $P^{VT2}$—$S^{VT2}$—.

In the formula, $R^{VT1}$ represents $P^{VT1}$—$S^{VT1}$— and $P^{VT1}$ and $P^{VT2}$ are each independently preferably Formula (R-1) or Formula (R-2).

In the formula, $S^{VT1}$ and $S^{VT2}$ are preferably a single bond or an alkylene group having 1 to 6 carbon atoms, and more preferably a single bond. In a case of emphasizing solubility with a liquid crystal composition, an alkylene group having 1 to 6 carbon atoms is preferable, an alkylene group having 1 to 3 carbon atoms is more preferable, an alkylene group having 1 to 2 carbon atoms is even more preferable, and one or two or more —CH$_2$— in the alkylene group may be substituted with —O—, —OCO—, or —COO—, provided that oxygen atoms are not directly adjacent to each other. In addition, at least, one of $S^{VT1}$ and $S^{VT2}$ present is a single bond, but it is preferable that all of $S^{VT1}$ and $S^{VT2}$ present are single bonds.

In the formula, $n^{VT1}$ is preferably an integer of 1 to 2, and $n^{VT2}$ is preferably an integer of 1 to 2. Here, $n^{VT1}+n^{VT2}$ is preferably an integer of 1 to 5, preferably an integer of 1 to 4, preferably an integer of 1 to 3, and more preferably an integer of 2 to 3.

In the formula, $m^{VT1}$ is preferably an integer of 1 to 3, and in a case of emphasizing the polymerization rate, $m^{VT1}$ is preferably an integer of 2 to 4 and $m^{VT1}$ is more preferably 2 or 3, and in a case of emphasizing compatibility with the liquid crystal composition, $m^{VT1}$ is preferably an integer of 0 to 2. Accordingly, it is particularly preferable that $m^{VT1}$ is 2 in order to achieve both polymerization rate and compatibility.

In the formula, $M^{VT1}$ is preferably a divalent cyclic group selected from a 1,4-phenylene group, a naphthalene-2,6-diyl group, and a phenanthrene-2,7-diyl group, and in a case where $n^{VT1}$ represents 2 or 3, and/or in a case where $m^{VT1}$ represents 0 and $n^{VT2}$ represents 2 or 3, further has a bond at an arbitrary position of the divalent cyclic group.

In the formula, $M^{VT2}$ is preferably a divalent cyclic group selected from a 1,4-phenylene group, a naphthalene-2,6-diyl group, and a phenanthrene-2,7-diyl group, and in a case where $n^{VT2}$ represents 2 or 3, $M^{VT2}$ to which $Z^{VT1}$ is linked further has a bond at an arbitrary position of the divalent cyclic group; however, $M^{VT2}$ to which $Z^{VT1}$ is not linked are independently selected from the divalent cyclic groups.

In the formula, at least one cyclic group of $M^{VT1}$ and $M^{VT2}$ present may be substituted with one or more alkyl groups having 1 to 12 carbon atoms, alkoxy groups having 1 to 12 carbon atoms, or halogens, and the alkyl group or alkoxy group is preferably an alkyl group or alkoxy group having 1 to 6 carbon atoms, preferably an alkyl group or alkoxy group having 1 to 5 carbon atoms, preferably an alkyl group or an alkoxy group having 1 to 4 carbon atoms, preferably an alkyl group or alkoxy group having 1 to 3 carbon atoms, preferably an alkyl group or alkoxy group having 1 to 2 carbon atoms, and particularly preferably an alkyl group or alkoxy group having 1 carbon atom.

$L^{VT1}$ is preferably a single bond, —OCH$_2$—, —CH$_2$O—, —C$_2$H$_4$—, —COO—, —OCO—, —CH=CR$^a$—COO—, —CH=CR$^a$—OCO—, —COO—CR$^a$=CH—, —OCO—CR$^a$=CH—, —(CH$_2$)$_Y$—COO—, —(CH$_2$)$_Y$—OCO—, —OCO—(CH$_2$)$_Y$—, —COO—(CH$_2$)$_Y$—, —CH=CH—, —CF$_2$O—, —OCF$_2$—, or —C≡C— (in the formula, R$^a$ each independently represent, a hydrogen atom or an alkyl group having 1 to 3 carbon atoms and, in the formula, Y represents an integer of 1 to 4), more preferably a single bond, —COO—, —OCO—, —CH=CH—COO—, —CH=CH—OCO—, —COO—CH=CH—, —OCO—CH=CH—, —(CH$_2$)$_2$—COO—, —(CH$_2$)$_2$—OCO—, —OCO—(CH$_2$)$_2$—, —COO—(CH$_2$)$_2$—, or —C≡C—, even more preferably —COO—, —OCO—, —CH=CH—COO—, —OCO—CH=CH—, —(CH$_2$)$_2$—COO—, or —OCO—(CH$_2$)$_2$—, and particularly preferably —(CH$_2$)$_2$—COO—, or —OCO—(CH$_2$)$_2$—.

It is preferable to contain one or two or more of polymerizable compounds represented by General Formula (VI-1) and General Formula (VI-2):

[Chem. 30]

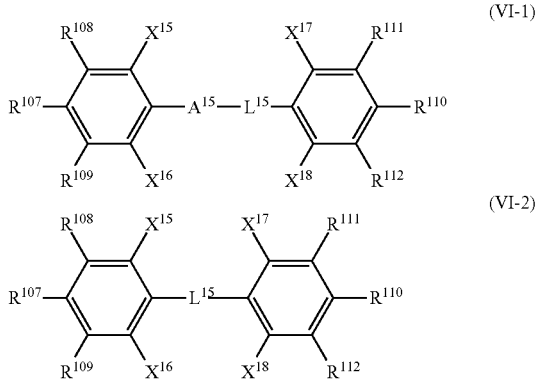

(VI-1)

(VI-2)

as the polymerizable compound represented by General Formula (VI).

In the formulas, $R^{107}$ represents $P^{107}$—$S^{107}$—, $R^{110}$ represents $P^{110}$—$S^{110}$—, and $P^{107}$ and $P^{110}$ each independently represents any one of the formulas (R-1) to (R-15), and $S^{107}$ and $S^{110}$ each independently represent a single bond or an alkylene group having 1 to 15 carbon atoms, and one or two or more —CH$_2$— in the alkylene group may be substituted with —O—, —OCO—, or —COO—, provided that the oxygen atoms are not directly adjacent to each other, but a single bond or an alkylene group having 1 to 6 carbon atoms is preferable (one or two or more —CH$_2$— in the alkylene group may be substituted with —O—, provided that the oxygen atoms are not directly adjacent to each other), and a single bond is particularly preferable. In the formulas, $R^{108}$, $R^{109}$, $R^{111}$, and $R^{112}$ each independently represent Formula (R-1) to Formula (R-15), an alkyl group having 1 to 3 carbon atoms, an alkoxy group having 1 to 3 carbon atoms, a fluorine atom, or a hydrogen atom, and $A^{15}$ represents a 1,4-phenylene group, a 1,4-cyclohexylene group, a pyridine-2,5-diyl group, a pyrimidine-2,5-diyl group, a naphthalene-2,6-diyl group, an indane-2,5-diyl group, a 1,2,3,4-tetrahydronaphthalene-2,6-diyl group, or a 1,3-dioxane-2,5-diyl group, but the group may be unsubstituted or substituted with an alkyl group having 1 to 12 carbon atoms, a halogen (a fluorine atom or a chlorine atom), a cyano group, or a nitro group, $L^{15}$ represents a single bond, —OCH$_2$—, —CH$_2$O—, —C$_2$H$_4$—, —COO—, —OCO—, —CH=CR$^a$—COO—, —CH=CR$^a$—OCO—, —COO—CR$^a$=CH—, —OCO—CR$^a$=CH—, —(CH$_2$)$_Y$—COO—, —(CH$_2$)$_Y$—OCO—, —OCO—(CH$_2$)$_Y$—, —COO—(CH$_2$)$_Y$—, —CH=CH—, —CF$_2$O—, —OCF$_2$—, or —C≡C— (where R$^a$ each independently represents a hydrogen atom or an alkyl group having 1 to 3 carbon atoms and Y represents an integer of 1 to 4).

In the formulas, $X^{15}$, $X^{16}$, $X^{17}$, and $X^{18}$ each independently represent a hydrogen atom, an alkyl group having 1 to 3 carbon atoms, or a fluorine atom.

The polymerizable compound represented by General Formula (VI-1) and General Formula (VI-2) is characterized by having a mesogen structure having two or three rings and it is possible to improve the compatibility with the liquid crystal composition by combined use with the polymerizable compound of General Formula (I-1) of the present invention.

The content of the polymerizable compound represented by General Formula (VI-1) and General Formula (VI-2) is contained in an amount of 0.01% to 5% by mass, but the lower limit value of the content is preferably 0.02% by mass, preferably 0.03% by mass, preferably 0.04% by mass, preferably 0.05% by mass, preferably 0.06% by mass, preferably 0.07% by mass, preferably 0.08% by mass, preferably 0.09% by mass, preferably 0.1% by mass, preferably 0.15% by mass, preferably 0.2% by mass, preferably 0.25% by mass, preferably 0.3% by mass, preferably 0.35% by mass, preferably 0.4% by mass, preferably 0.5% by mass, and preferably 0.55% by mass, and the upper limit value of the content is preferably 4.5% by mass, preferably 4% by mass, preferably 3.5% by mass, preferably 3% by mass, preferably 2.5% by mass, preferably 2% by mass, preferably 1.5% by mass, preferably 1% by mass, preferably 0.95% by mass, preferably 0.9% by mass, preferably 0.85% by mass, preferably 0.8% by mass, preferably 0.75% by mass, preferably 0.7% by mass, preferably 0.65% by mass, preferably 0.6% by mass, and preferably 0.55% by mass.

As the compound represented by General Formula (VI-2), if is preferable to contain one or two or more of polymerizable compounds represented by General Formula (IV).

[Chem. 31]

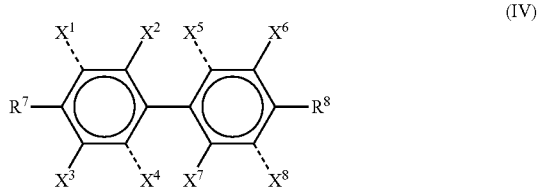

(IV)

In the formula, $R^7$ and $R^8$ each independently represents any one of the formulas (R-1) to (R-15), and $X^1$ to $X^8$ each independently represent a trifluoromethyl group, a trifluoromethoxy group, a fluorine atom, or a hydrogen atom.

[Chem. 32]

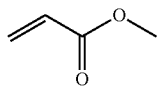
(R-1)

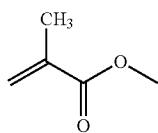
(R-2)

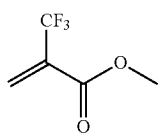
(R-3)

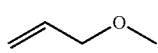
(R-4)

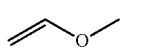
(R-5)

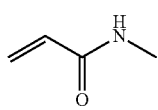
(R-6)

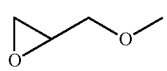
(R-7)

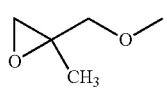
(R-8)

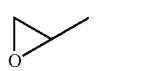
(R-9)

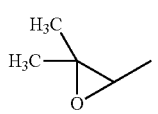
(R-10)

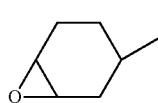
(R-11)

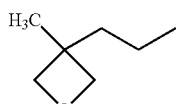
(R-12)

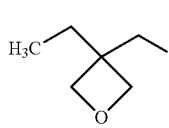
(R-13)

-continued

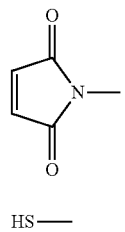
(R-14)

HS—
(R-15)

The structure of the biphenyl skeleton in General Formula (IV) is preferably that in Formula (IV-11) to Formula (IV-14), and particularly preferably that in Formula (IV-11).

[Chem. 33]

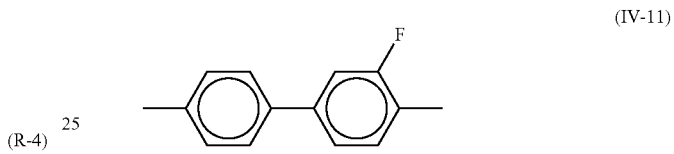
(IV-11)

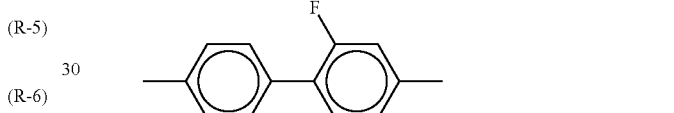
(IV-12)

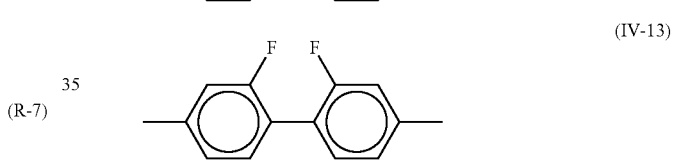
(IV-13)

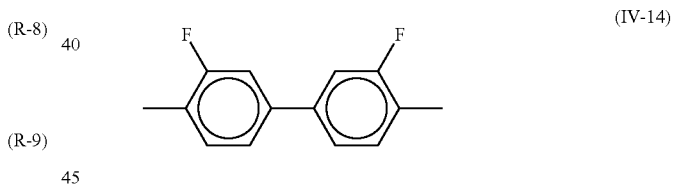
(IV-14)

The polymerizable compound including the skeleton represented by Formula (IV-11) to Formula (IV-14) has an optimum alignment regulating force after polymerization and is able to obtain a good alignment state.

Specifically, for example, the compound represented by General Formula (VI-2) is preferably a compound represented by Formula (XX-1) to General Formula (XX-10), and a compound represented by Formula (XX-1) to Formula (XX-4) is more preferable.

[Chem. 34]

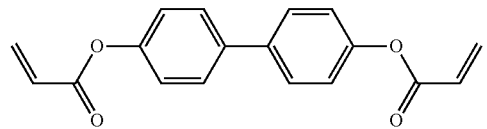
(XX-1)

(XX-2)
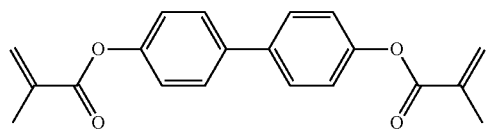

(XX-3)
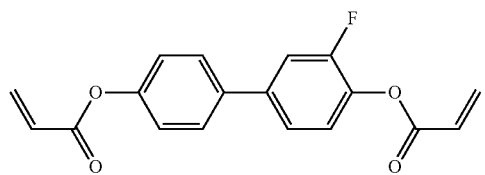

(XX-4)
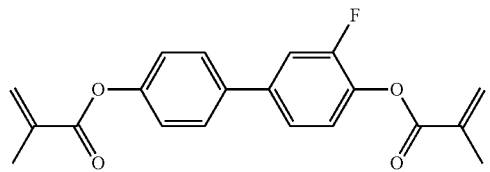

(XX-5)
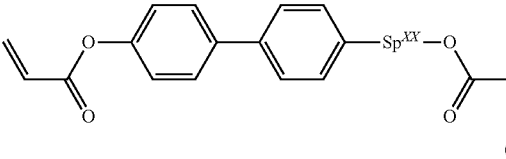

(XX-6)
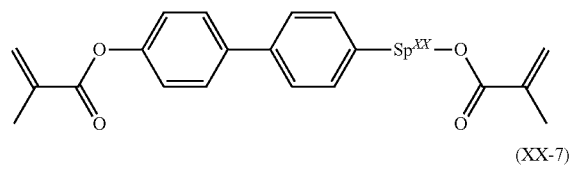

(XX-7)
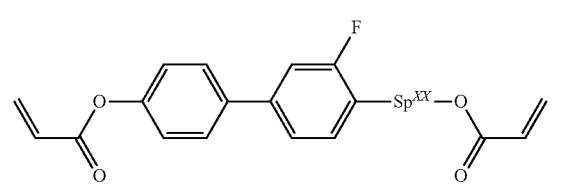

(XX-8)
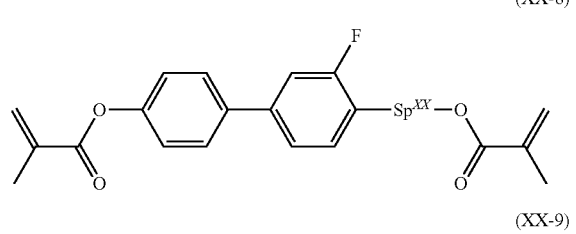

(XX-9)
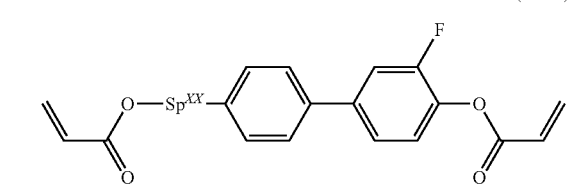

(XX-10)
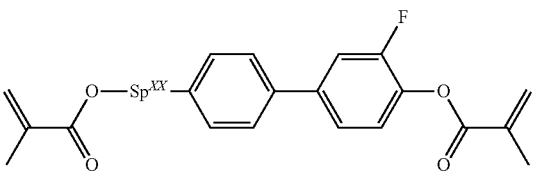

In Formula (XX-1) to General Formula (XX-10), Sp$^{xx}$ represents an alkylene group having 1 to 8 carbon atoms or —O—(CH$_2$)$_s$— (where s represents an integer of 2 to 7, and an oxygen atom is bonded to a ring).

In Formula (XX-1) to General Formula (XX-10), the hydrogen atom in the 1,4-phenylene group may be further substituted with any of —F, —Cl, —CF$_3$, —CH$_3$, or Formula (R-1) to Formula (R-15).

In addition, as the compound represented by General Formula (VI-1), for example, a polymerizable compound such as Formula (M31) to Formula (M48) is preferable.

[Chem. 35]

(M31)
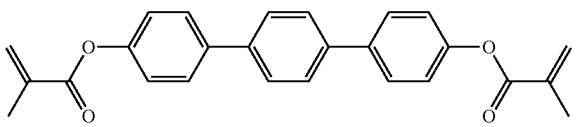

(M32)
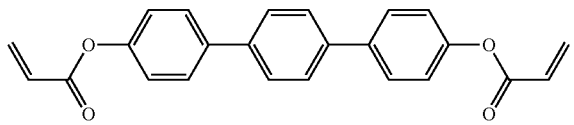

(M33)
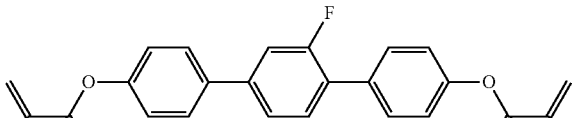

(M34)
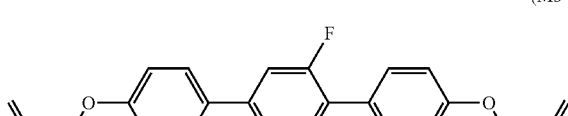

(M35)
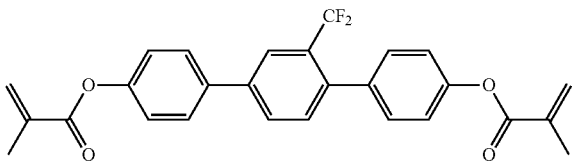

(M36)
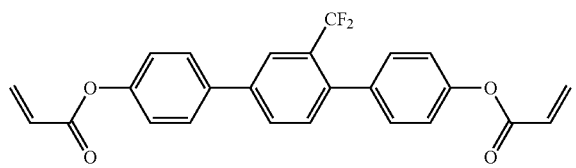
(M37)
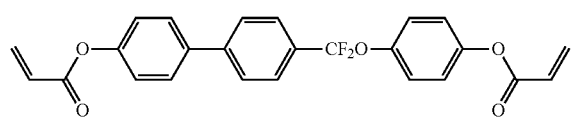
(M38)
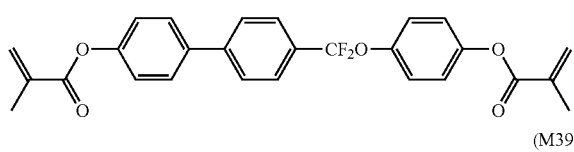
(M39)
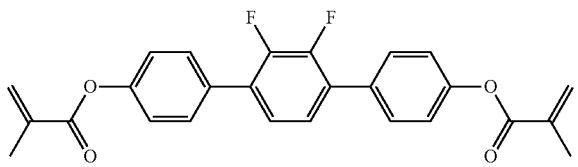
(M40)
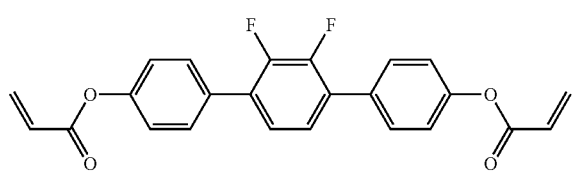
(M41)
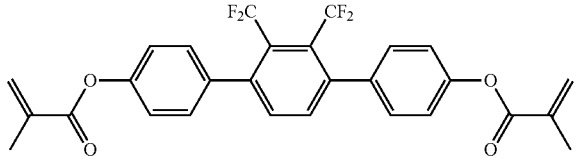
(M42)
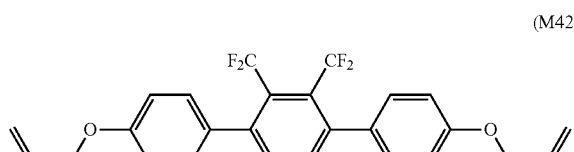
(M43)
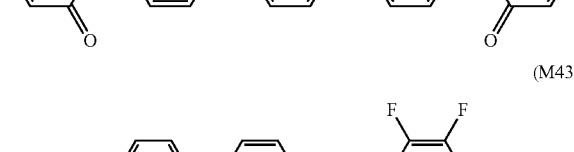
(M44)
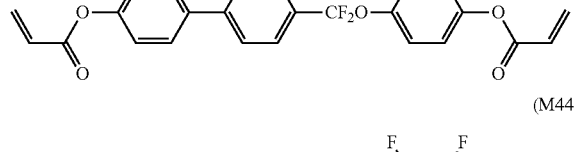, 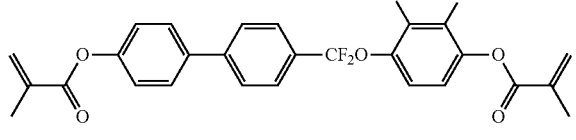
(M45)
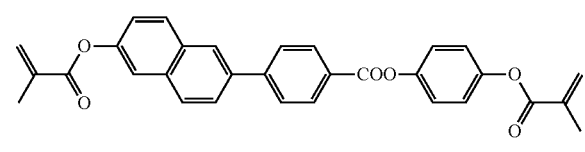
(M46)
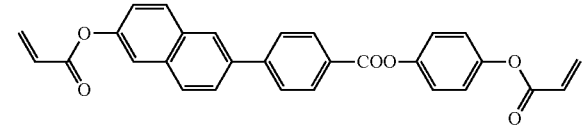
(M47)
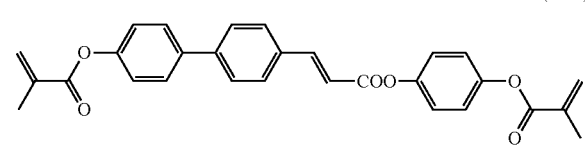
(M48)
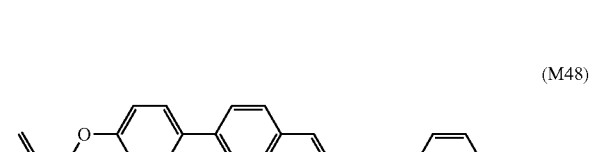
In addition, polymerizable compounds such as Formula (M301) to Formula (M316) are also preferable.
[Chem. 36]
(M301)
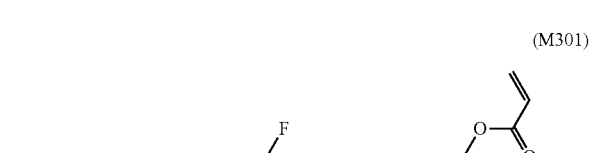
(M302)
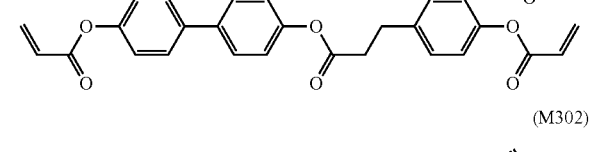
(M303)
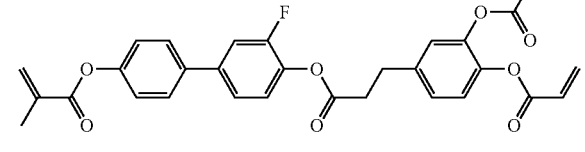
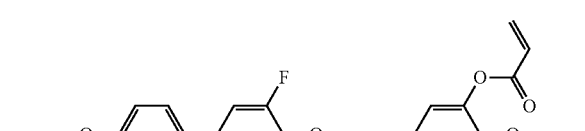
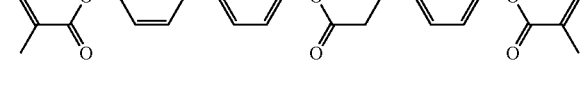

(M304)
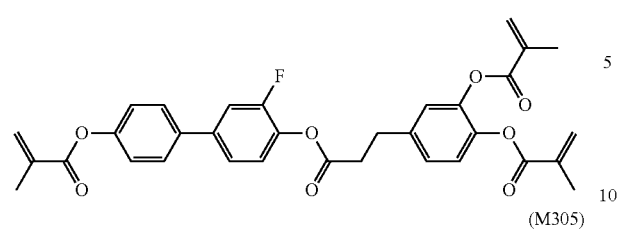
(M305)
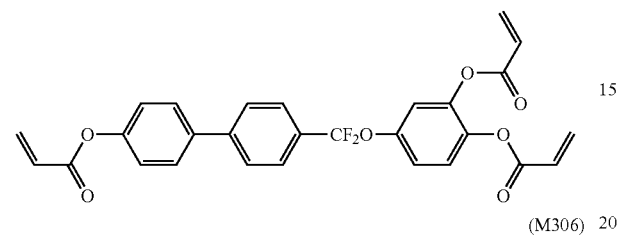
(M306)
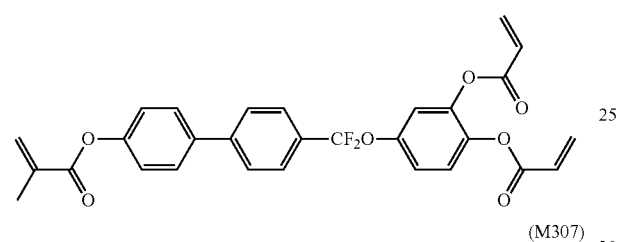
(M307)
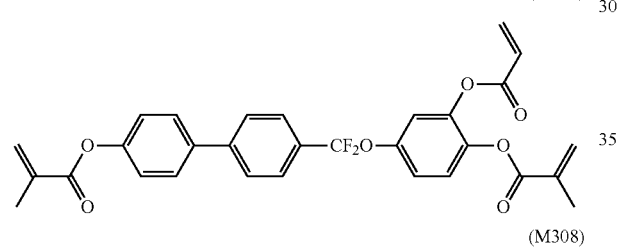
(M308)
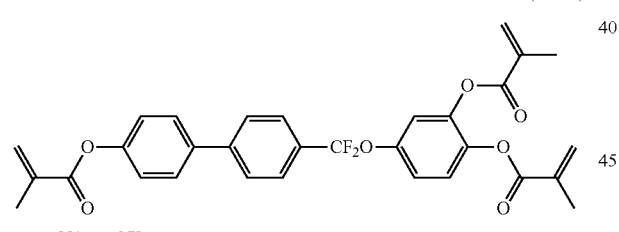
[Chem. 37]
(M309)
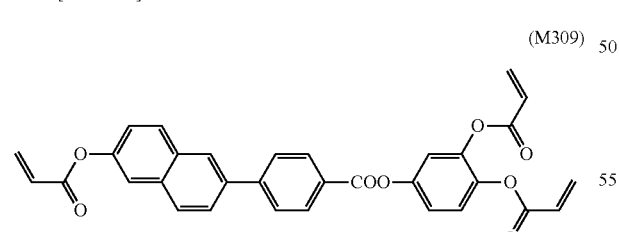
(M310)
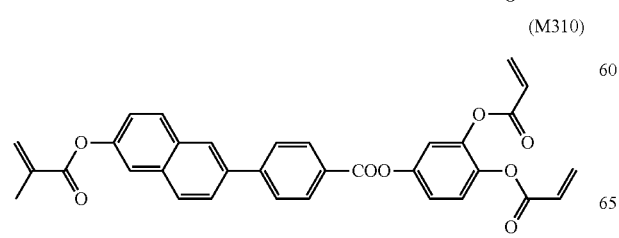
(M311)
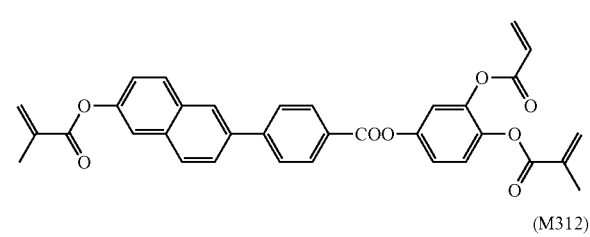
(M312)
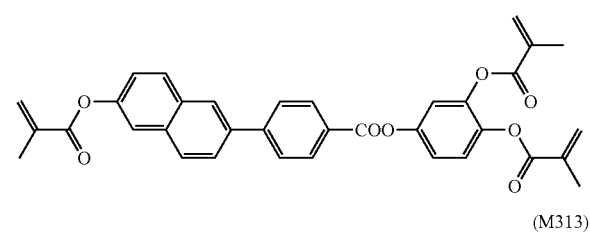
(M313)
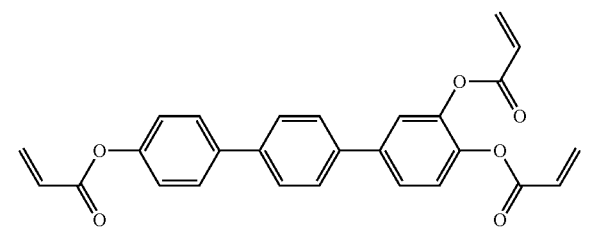
(M314)
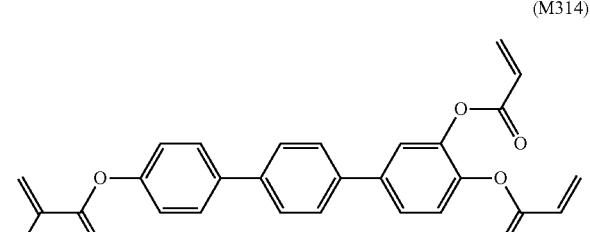
(M315)
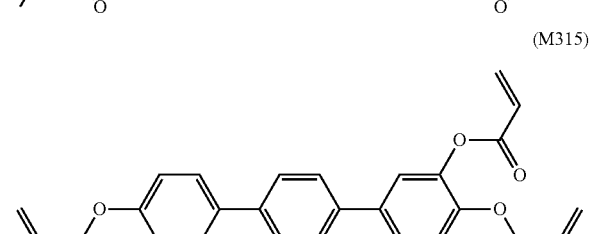
(M316)
The hydrogen atom in the 1,4-phenylene group and the naphthalene group in Formula (M301) to Formula (M316) may be further substituted with —F, —Cl, —CF$_3$, or —CH$_3$.
Polymerizable compounds such as Formula (VIa-1) to Formula (VIa-31) are also preferable.

[Chem. 38]
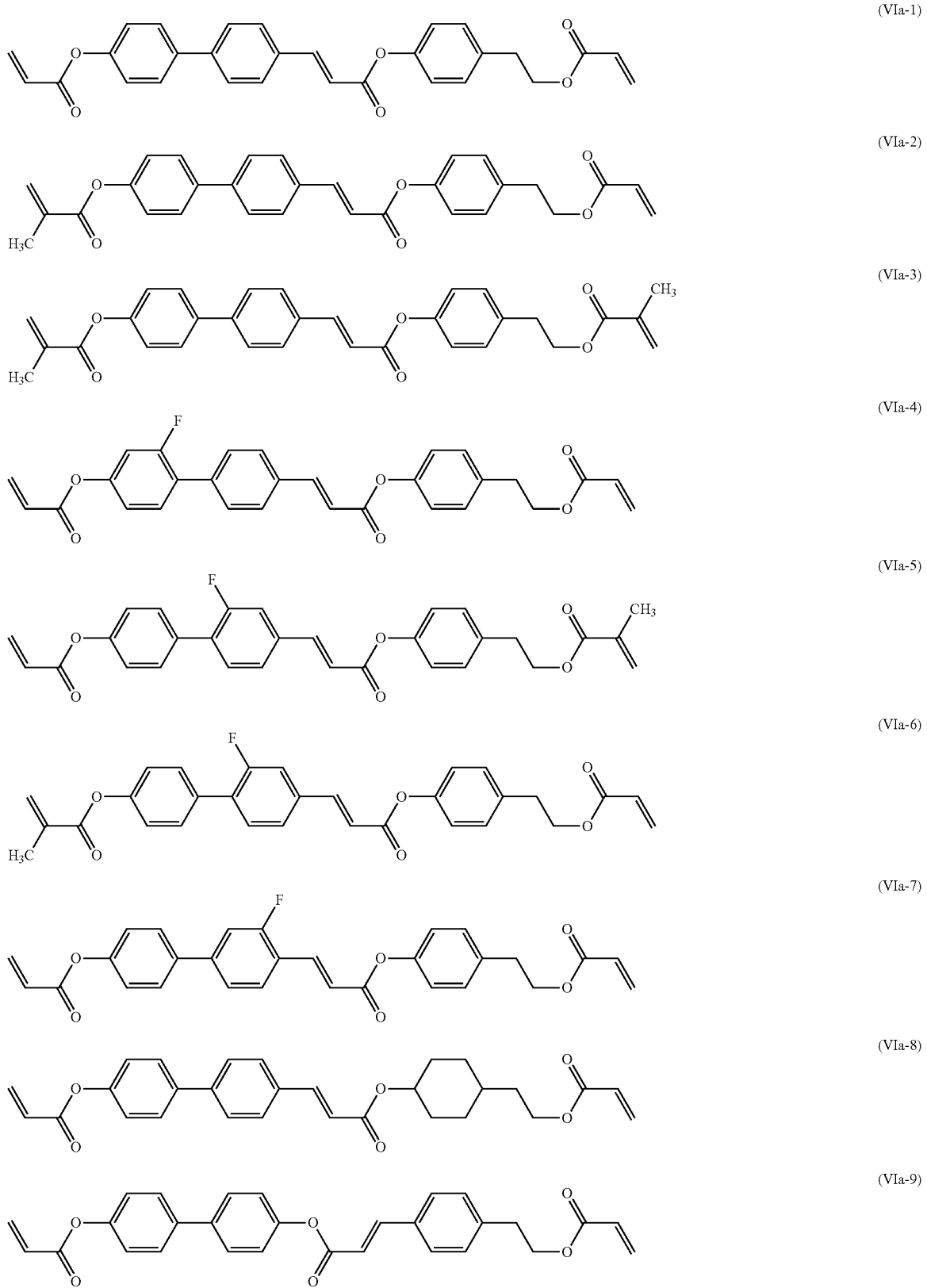
(VIa-1)
(VIa-2)
(VIa-3)
(VIa-4)
(VIa-5)
(VIa-6)
(VIa-7)
(VIa-8)
(VIa-9)

(VIa-10)
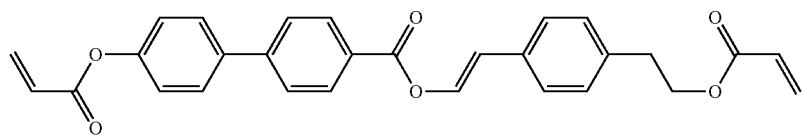
(VIa-11)
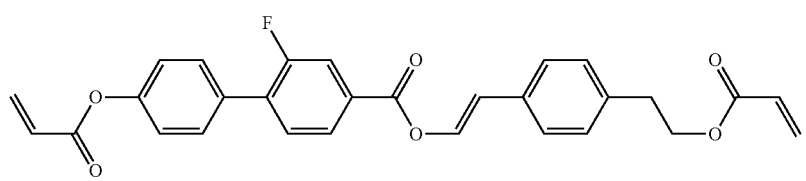
(VIa-12)
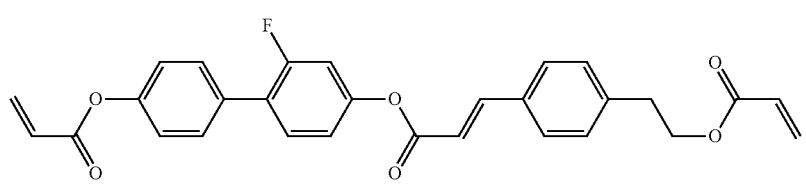
(VIa-13)
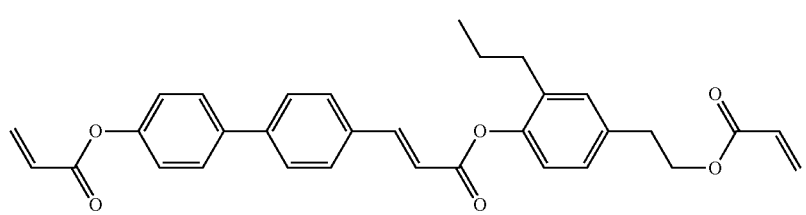
[Chem. 39]
(VIa-14)
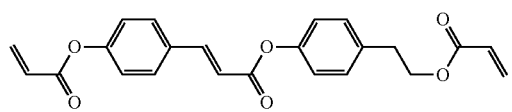
(VIa-15)
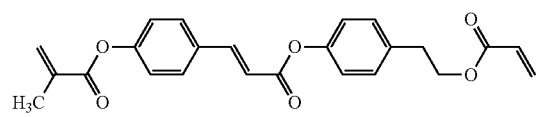
(VIa-16) (VIa-17)
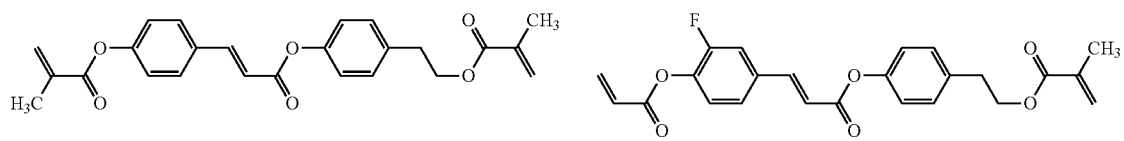
(VIa-18)
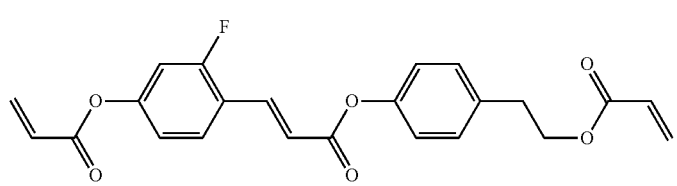
[Chem. 40]
(VIa-19)
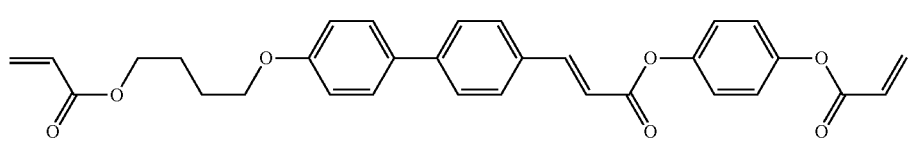
(VIa-20)
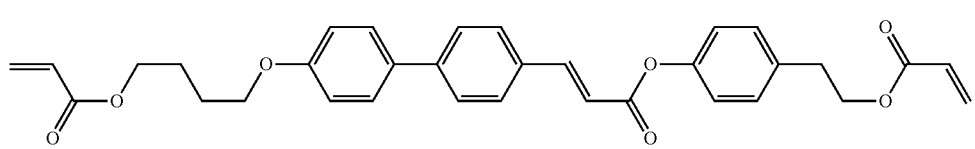

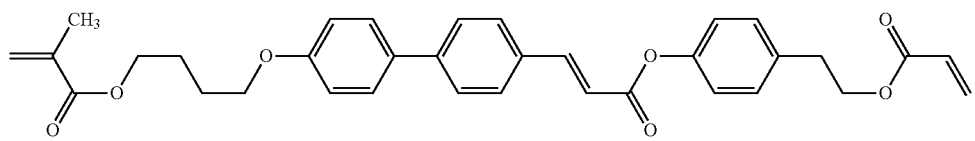
(VIa-21)
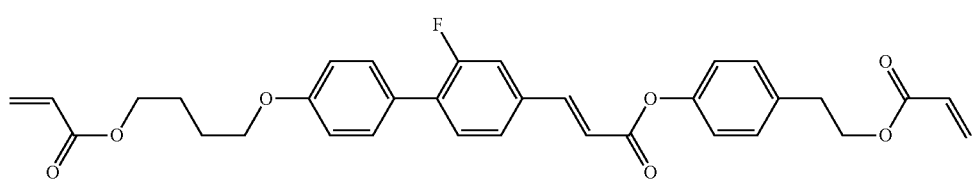
(VIa-22)
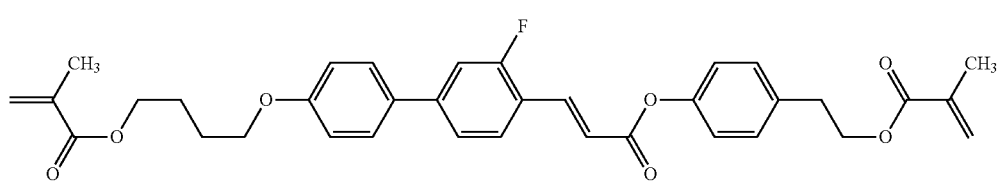
(VIa-23)
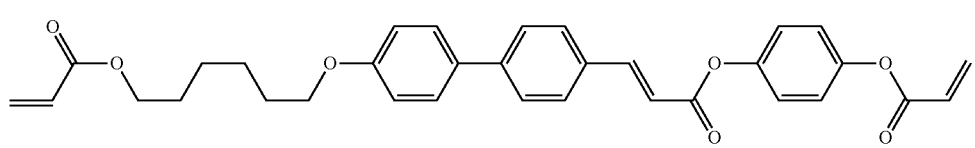
(VIa-24)
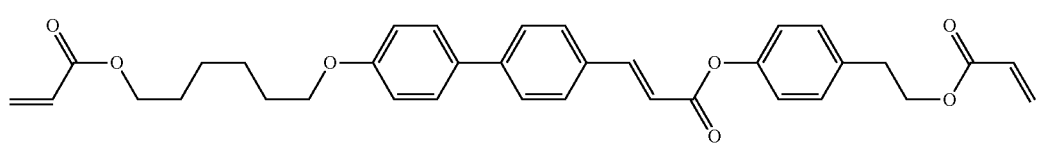
(VIa-25)
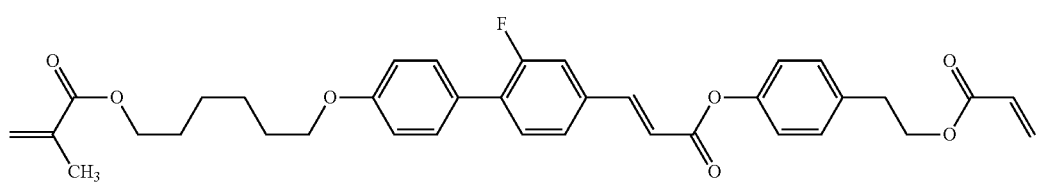
(VIa-26)
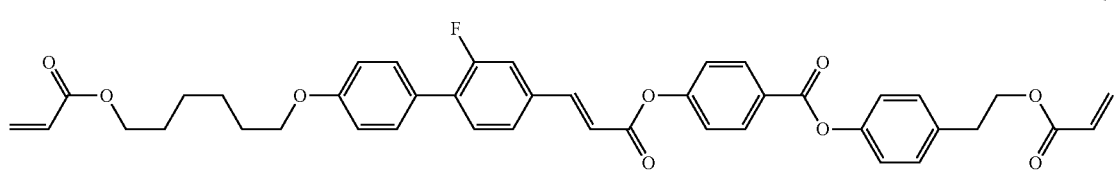
(VIa-27)
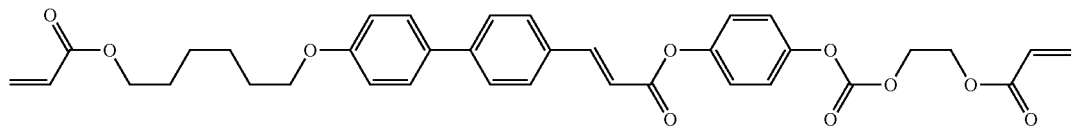
(VIa-28)
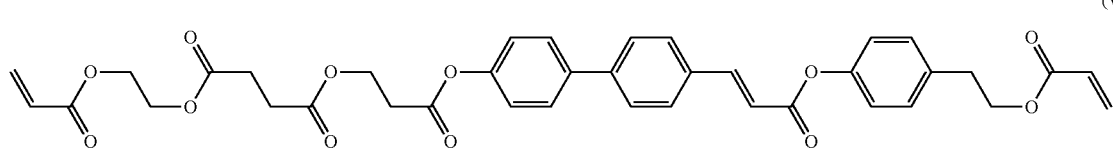
(VIa-29)

(VIa-30)

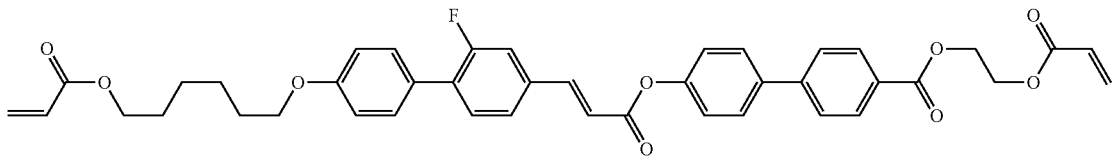

[Chem. 41]

(VIa-31)

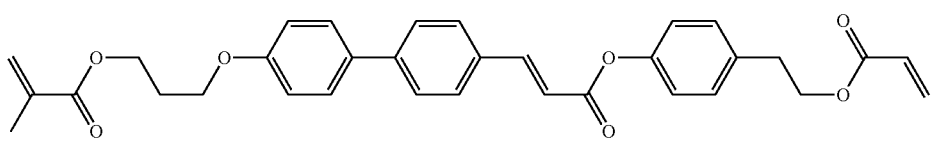

Since a liquid crystal composition having a negative dielectric anisotropy and containing a compound represented by General Formula (i) of the present invention and General Formula (I-1) which is a polymerizable compound at the same time is able to obtain a low viscosity ($\eta$), a low rotational viscosity ($\gamma_1$), and a large elastic constant ($K_{33}$), it is possible for a PSA mode or PSVA mode liquid crystal display element using the liquid crystal composition to realize a high-speed response.

In addition, the antioxidant is preferably a hindered phenol represented by General Formula (H-1) to General Formula (H-4).

[Chem. 42]

(H-1)

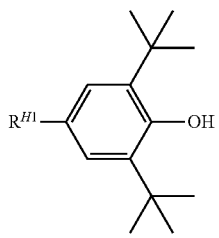

(H-2)

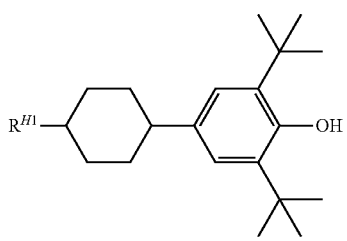

(H-3)

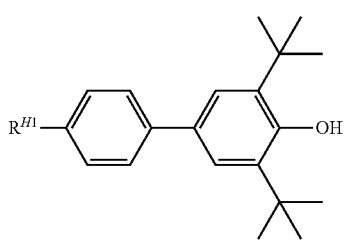

(H-4)

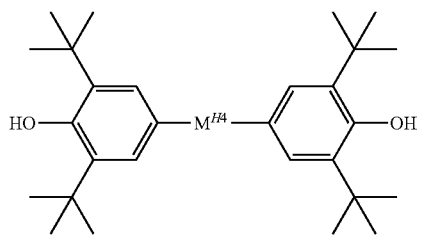

In General Formula (H-1) to General Formula (H-4), $R^{H1}$ represents an alkyl group having 1 to 10 carbon atoms, an alkoxyl group having 1 to 10 carbon atoms, an alkenyl group having 2 to 10 carbon atoms, or an alkenyloxy group having 2 to 10 carbon atoms, but one —$CH_2$— or two or more non-adjacent —$CH_2$— present in the group may each independently be substituted with —O— or —S—, in addition, one or two or more hydrogen atoms present in the group may each independently be substituted with a fluorine atom or a chlorine atom. More specifically, an alkyl group having 2 to 7 carbon atoms, an alkoxyl group having 2 to 7 carbon atoms, an alkenyl group having 2 to 7 carbon atoms, or an alkenyloxy group having 2 to 7 carbon atoms is preferable, and an alkyl group having 3 to 7 carbon atoms or an alkenyl group having 2 to 7 carbon atoms is more preferable.

In General Formula (H-4), $M^{H4}$ represents an alkylene group having 1 to 15 carbon atoms (one or two or more —$CH_2$— in the alkylene group may be substituted with —O—, —CO—, —COO—, or —OCO—, provided that the oxygen atoms are not directly adjacent to each other) —$OCH_2$—, —$CH_2O$—, —COO—, —OCO—, —$CF_2O$—, —$OCF_2$—, —$CF_2CF_2$—, —CH=CH—COO—, —CH=CH—OCO—, —COO—CH=CH—, —OCO—CH=CH—, —CH=CH—, —C≡C—, a single bond, a 1,4-phenylene group (an arbitrary hydrogen atom in the 1,4-phenylene group may be substituted with a fluorine atom), or a trans-1,4-cyclohexylene group, but an alkylene group having 1 to 14 carbon atoms is preferable, and, in consideration of the volatility, it is preferable that the number of carbon atoms is large, while, in consideration of the viscosity, the number of carbon atoms is preferably not excessively large, thus 2 to 12 carbon atoms is more preferable, 3 to 10 carbon atoms is more preferable, 4 to 10 carbon atoms is more preferable, 5 to 10 carbon atoms is more preferable, and 6 to 10 carbon atoms is more preferable.

In General Formula (H-1) to General Formula (H-4), one or two or more non-adjacent —CH= in the 1,4-phenylene group may be substituted with —N=. In addition, the hydrogen atoms in the 1,4-phenylene group may each independently be substituted with a fluorine atom or a chlorine atom.

In General Formula (H-1) to General Formula (H-4), one or two or more non-adjacent —CH$_2$— in the 1,4-cyclohexylene group may be substituted with —O— or —S—. In addition, the hydrogen atoms in the 1,4-cyclohexylene group may each independently be substituted with a fluorine atom or a chlorine atom.

More specific examples thereof include Formula (H-11) to Formula (H-15).

[Chem. 43]

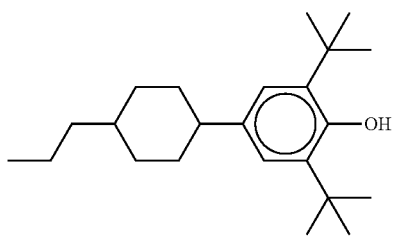

(H-11)

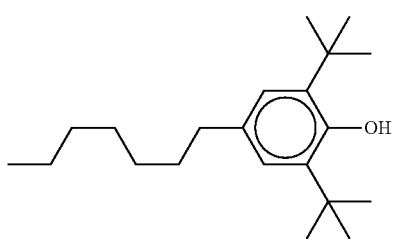

(H-12)

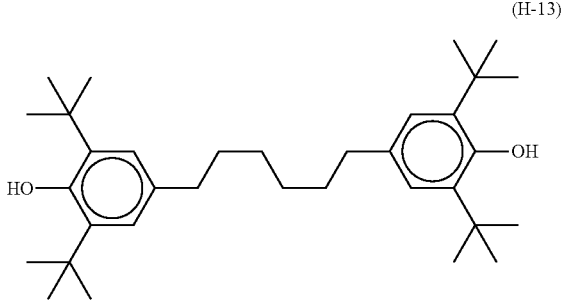

(H-13)

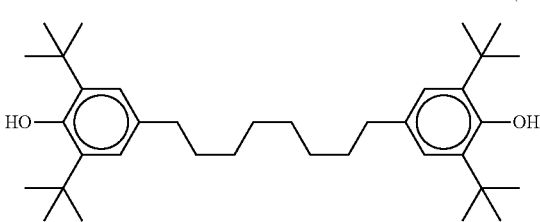

(H-14)

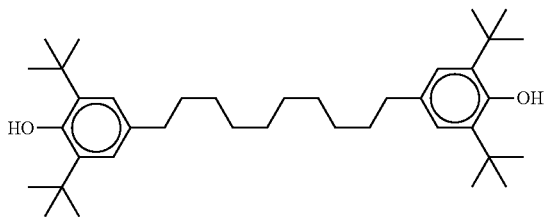

(H-15)

The liquid crystal composition of the present invention may contain an antioxidant in an amount of 1 mass ppm or more, preferably 10 mass ppm or more, preferably 20 mass ppm or more, and preferably 50 mass ppm or more. The upper limit value of the content of the antioxidant is 10,000 ppm by mass, preferably 1,000 ppm by mass, preferably 500 ppm by mass, and preferably 100 ppm by mass.

In the present Invention, it is possible to produce the compound represented by General Formula (i) as follows. Naturally, the gist and scope of the present invention are not limited by these production examples.

(Production Method 1)

By reacting a compound represented by General Formula (i-1):

[Chem. 44]

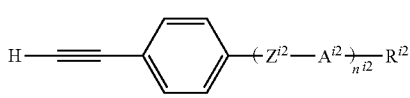

(i-1)

(in the formula, $A^{i2}$, $Z^{i2}$, $n^{i2}$, and $R^{i2}$ have the same meanings as $A^{i2}$, $Z^{i2}$, $n^{i2}$, and $R^{i2}$ in General Formula (i), respectively) and a compound represented by General Formula (i-2):

[Chem. 45]

(i-2)

(in the formula, $X^1$ and $X^2$ each independently represent a chlorine atom, a bromine atom, an iodine atom, or a trifluoromethanesulfonyloxy group), in the presence of a transition metal catalyst, a copper catalyst, and a base in an organic solvent, it is possible to obtain a compound represented by General Formula (i-3):

[Chem. 46]

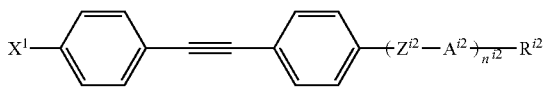

(i-3)

(in the formula, $A^{i2}$, $Z^{i2}$, $n^{i2}$ and $R^{i2}$ have the same meanings as $A^{i2}$, $Z^{i2}$, $n^{i2}$ and $R^{i2}$ in General Formula (i), respectively, and $X^1$ represents a chlorine atom, a bromine atom, an iodine atom, or a trifluoromethanesulfonyloxy group).

As the organic solvent to be used, any solvent may be used as long as the reaction is able to proceed suitably, but ether solvents such as diethyl ether, diisopropyl ether or tetrahydrofuran or amide solvents such as N,N-dimethylformamide, N,N-dimethylacetamide or N-methylpyrrolidinone are preferable, and tetrahydrofuran, N,N-dimethylformamide, N,N-dimethylacetamide, or N-methylpyrrolidinone is particularly preferable. In addition, a plurality of solvents may be mixed as necessary.

The reaction temperature may be any as long as the reaction is able to proceed suitably, but a temperature from room temperature to the temperature at which reflux of the organic solvent occurs is preferable, a temperature from 40° C. to the temperature at which reflux of the organic solvent occurs is more preferable, and a temperature from 60° C. to the temperature at which the reflux of the solvent occurs is particularly preferable.

As the copper catalyst to be used, any copper may be used as long as the reaction is able to proceed suitably, but copper (I) chloride, copper (1) bromide, or copper (I) iodide is preferable, and copper (I) iodide is more preferable.

The transition metal catalyst to be used may be any as long as the reaction is able to proceed suitably, but it is preferable to use palladium-based transition metal catalysts or nickel-based transition metal catalysts such as tetrakis (triphenylphosphine) palladium (0), palladium (II) acetate, bis(triphenylphosphine) palladium (II) dichloride, [1,1'-bis (diphenylphosphino) ferrocene] palladium (II) dichloride, or bis[di-tert-butyl (4-dimethylaminophenyl) phosphine] palladium (II) dichloride, and tetrakis(triphenylphosphine) palladium (0), palladium acetate (II), bis[di-tert-butyl (4-dimethylaminophenyl) phosphine] palladium (II) dichloride or [1,1'-bis(diphenylphosphino) ferrocene] palladium (II) dichloride is more preferable. In addition, in order to promote the progress of the reaction, a phosphine ligand may be added as necessary.

Any base may be used as long as the reaction is able to proceed suitably, and aqueous ammonia, amine reagents such as triethylamine or diisopropylamine, pyridine reagents such as pyridine or 2,6-dimethylpyridine, carbonates such as carbonate potassium, potassium hydrogen carbonate, sodium carbonate, or cesium carbonate are preferable, and triethylamine and diisopropylamine are more preferable.

In order to efficiently obtain the targeted compound represented by General Formula (i-3), $X^1$ and $X^2$ in General Formula (i-2) are preferably different. Subsequently, by reacting the compound represented by General Formula (i-3) with the compound represented by General Formula (i-4):

[Chem. 47]

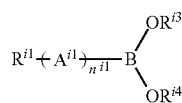

(i-4)

(in the formula, $A^{i1}$, $n^{i1}$, and $R^{i1}$ have the same meanings as $A^{i1}$, $n^{i1}$, and $R^{i1}$ in General Formula (i), respectively, and $R^{i3}$ and $R^{i4}$ each independently represent an alkyl group having 1 to 5 carbon atoms which may be linear or branched) in the presence of a transition metal catalyst and a base in an organic solvent, it is possible to obtain the compound represented by General Formula (i-5):

[Chem. 48]

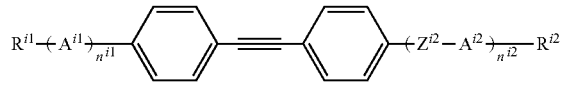

(i-5)

(in the formula, $A^{i1}$, $A^{i2}$, $Z^{i2}$, $R^{i1}$, $R^{i2}$, $n^{i2}$, and $n^{i1}$ have the same meanings as $A^{i1}$, $A^{i2}$, $Z^{i2}$, $R^{i1}$, $R^{i2}$, $n^{i2}$, and $n^{i1}$ in General Formula (i), respectively).

As the organic solvent to be used, any solvent may be used as long as the reaction is able to proceed suitably, but ether solvents such as diethyl ether, diisopropyl ether, 1,4-dioxane, or tetrahydrofuran, hydrocarbon-based solvents such as hexane, heptane, toluene, or xylene, amide solvents such as N-methylpyrrolidinones such as N,N-dimethylformamide and N,N-dimethylacetamide, alcohol-based solvents such as methanol, ethanol, propanol, or isopropyl alcohol are preferable, and 1,4-dioxane, tetrahydrofuran, methanol, and ethanol are more preferable.

The reaction temperature may be any temperature as long as the reaction is able to proceed suitably, but is preferably a temperature from room temperature to the temperature at which reflux of the organic solvent occurs, more preferably a temperature from 40° C. to the temperature at which reflux of the organic solvent occurs, and particularly preferably a temperature from 60° C. to the temperature at which reflux of the organic solvent occurs.

The transition metal catalyst to be used may be any as long as the reaction is able to proceed suitably, but it is preferable to use palladium-based transition metal catalysts or nickel-based transition metal catalysts such as tetrakis (triphenylphosphine) palladium (0), palladium (II) acetate, bis(triphenylphosphine) palladium (II) dichloride, [1,1'-bis (diphenylphosphino) ferrocene] palladium (II) dichloride, or bis[di-tert-butyl (4-dimethylaminophenyl) phosphine] palladium (II) dichloride, and tetrakis(triphenylphosphine) palladium (0), palladium (II) acetate, bis[di-tert-butyl (4-dimethylaminophenyl) phosphine] palladium (II) dichloride or [1,1'-bis(diphenylphosphino) ferrocene] palladium (II) dichloride is more preferable. In addition, in order to promote the progress of the reaction, a phosphine ligand may be added as necessary.

Any base may be used as long as the reaction is able to proceed suitably, and alkali metal hydroxides such as sodium hydroxide and potassium hydroxide, carbonates such as sodium carbonate, sodium hydrogen carbonate, potassium, carbonate, potassium hydrogen-carbonate, and cesium carbonate are preferable, and potassium carbonate or cesium carbonate are more preferable. In addition, it is also preferable to use as an aqueous solution as necessary.

Subsequently, reacting the compound represented by General Formula (i-5) with hydrogen gas in an organic solvent in the presence of a metal catalyst makes it possible to obtain a compound represented by General Formula (i).

As the organic solvent to be used, any organic solvent may be used as long as the reaction is able to proceed suitably, but ether solvents such as diisopropyl ether, diethyl ether, 1,4-dioxane or tetrahydrofuran, hydrocarbon solvents such as hexane, heptane, toluene, or xylene, alcohol-based solvents such as methanol, ethanol, propanol, isopropyl alcohol, or butanol, ester-based solvents such as ethyl acetate or butyl acetate are preferable, and tetrahydrofuran, hexane, heptane, toluene, ethanol, or ethyl acetate is preferable. It is also preferable to add an acid such as hydrochloric acid, acetic acid, or sulfuric acid as necessary.

The reaction temperature may be any temperature as long as the reaction proceeds suitably, but is preferably 0° C. to 80° C., and more preferably room temperature to 60° C.

As the metal catalyst to be used, any metal catalyst may be used as long as the reaction proceeds suitably, but palladium carbon, ruthenium carbon, platinum black, or platinum oxide is preferable, and palladium carbon is more preferable.

The hydrogen pressure during the reaction may be any as long as the reaction proceeds suitably, but is preferably from atmospheric pressure to 0.5 MPa, and more preferably from 0.2 MPa to 0.5 MPa.

(Production Method 2)

By reacting the compound represented by General Formula (i-6):

[Chem. 49]

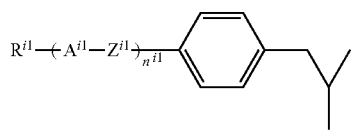

(i-6)

(in the formula, $A^{i1}$, $Z^{i1}$, $n^{i1}$ and $R^{i1}$ have the same meanings as $A^{i1}$, $Z^{i1}$, $n^{i1}$ and $R^{i1}$ in General Formula (i), respectively, and Y each independently represents a chlorine atom, a bromine atom, or an iodine atom) with triphenylphosphine in an organic solvent or in the absence of a solvent, it is possible to obtain the compound represented by General Formula (i-7):

[Chem. 50]

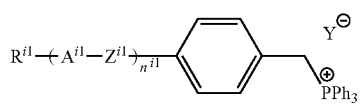

(i-7)

(in the formula, $A^{i1}$, $Z^{i1}$, $n^{i1}$, and $R^{i1}$ have the same meanings as $A^{i1}$, $Z^{i1}$, $n^{i1}$ and $R^{i1}$ in General Formula (i), respectively, Y each independently represents a chlorine atom, a bromine atom, or an iodine atom, and Ph represents a phenyl group).

In a case of using an organic solvent, any solvent may be used as long as the reaction proceeds suitably, but a saturated hydrocarbon solvent such as hexane, heptane, cyclohexane, or methylcyclohexane, an aromatic solvent such as toluene, xylene, or mesitylene, an ether solvent such as diethyl ether, diisopropyl ether, tetrahydrofuran, or 1,4-dioxane, an amide solvent such as N-methylpyrrolidinones such as N,N-dimethylformamide, and N,N-dimethylacetamide are preferable, a saturated hydrocarbon solvent or an aromatic solvent is more preferable, and toluene or xylene is particularly preferable.

The reaction temperature may be any temperature as long as the reaction proceeds suitably, but is preferably a temperature from room temperature to the temperature at which reflux of the organic solvent occurs, more preferably a temperature from 50° C. to the temperature at which reflux of the organic solvent occurs, and particularly preferably a temperature from 90° C. to the temperature at which reflux of the organic solvent occurs.

Subsequently, a compound represented by General Formula (i-7) is reacted with a base in an organic solvent to prepare a phosphorus ylide reagent, then, by reaction with the compound represented by General Formula (i-8):

[Chem. 51]

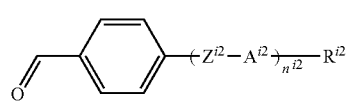

(i-8)

(in the formula, $A^{i2}$, $Z^{i2}$, $n^{i2}$, and $R^{i2}$ have the same meanings as $A^{i2}$, $Z^{i2}$, $n^{i2}$, and $R^{i2}$ in General Formula (i), respectively), it is possible to obtain the compound represented by General Formula (i-9):

[Chem. 52]

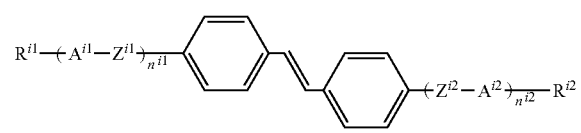

(i-9)

(in the formula, $A^{i1}$, $A^{i2}$, $Z^{i1}$, $Z^{i2}$, $R^{i1}$, $R^{i2}$, $n^{i2}$, and $n^{i1}$ have the same meanings as $A^{i1}$, $A^{i2}$, $Z^{i1}$, $Z^{i2}$, $R^{i1}$, $R^{i2}$, $n^{i2}$, and $n^{i1}$ in General Formula (i), respectively).

As the organic solvent to be used, any solvent may be used as long as the reaction proceeds suitably, but ether solvents such as diethyl ether, diisopropyl ether, tetrahydrofuran, or 1,4-dioxane, and hydrocarbon solvents such as hexane, heptane, cyclohexane, methylcyclohexane, toluene, or xylene are preferable, and tetrahydrofuran is preferable. In addition, it is also preferable to use a mixture of a plurality of solvents as necessary.

The reaction temperature may be any temperature as long as the reaction proceeds suitably, but is preferably −60° C. to 20° C., and more preferably −40° C. to 0° C.

Any base may be used as long as the reaction proceeds suitably, but hydroxide salts such as sodium hydroxide and potassium hydroxide, alkoxide reagents such as sodium methoxide, sodium ethoxide, or potassium tertiary butoxide, alkyl lithium reagents such as butyl lithium, secondary butyl lithium, or tertiary butyl lithium, and sodium hydride are preferable, and potassium hydroxide, potassium tertiary butoxide, sodium hydride, and butyl lithium are more preferable. Subsequently, reacting the compound represented by General Formula (i-9) with hydrogen gas in an organic solvent in the presence of a metal catalyst makes it possible to obtain a compound represented by General Formula (i).

As the organic solvent to be used, any solvent may be used as long as the reaction proceeds suitably, but ether solvents such as diisopropyl ether, diethyl ether, 1,4-dioxane, or tetrahydrofuran, hydrocarbon solvents such as hexane, heptane, toluene, or xylene, alcohol-based solvents such as methanol, ethanol, propanol, isopropyl alcohol, or butanol, and ester-based solvents such as ethyl acetate or butyl acetate are preferable, and tetrahydrofuran, hexane, heptane, toluene, ethanol, or ethyl acetate is preferable. In addition, it is also preferable to add an acid such as hydrochloric acid, acetic acid, or sulfuric acid as necessary.

The reaction temperature may be any temperature as long as the reaction proceeds suitably, but is preferably 0° C. to 80° C., and more preferably room temperature to 60° C.

As the metal catalyst to be used, any metal catalyst may be used as long as the reaction proceeds suitably, but palladium carbon, ruthenium carbon, platinum black or platinum oxide is preferable, and palladium carbon is more preferable.

The hydrogen pressure during the reaction may be any pressure as long as the reaction proceeds suitably, but is preferably atmospheric pressure to 0.5 MPa, and more preferably 0.2 MPa to 0.5 MPa.

A liquid crystal display element using the liquid crystal composition of the present invention has excellent display quality in which display defects are absent, or suppressed and has a fast response speed and, in particular, is applicable to VA type systems, PSVA type systems, PSA type systems, FFS type systems, IPS type systems, or ECB type systems, which are active matrix driven.

EXAMPLES

More detailed description will be given below of the present invention with reference to Examples, but the present invention is not limited to these Examples. In addition, in the compositions of the following Examples and Comparative Examples, "%" means "% by mass". The phase transition temperature was measured using a polarizing microscope provided with a temperature control stage and a differential scanning calorimeter (DSC) in combination.

The following abbreviations are used in the descriptions with respect to the compounds.
DMF: N,N-dimethylformamide
THF: tetrahydrofuran
Me: methyl group, Et: ethyl group, Pr: n-propyl group
In addition, in the examples, the following abbreviations are used for describing the compounds.
(Side Chain)
-n —$C_nH_{2n+1}$ linear alkyl group having n carbon atoms
n- $C_nH_{n+1}$— linear alkyl group having n carbon atoms
—On —$OC_nH_{2n+1}$ linear alkoxyl group having n carbon atoms
nO— —$C_nH_{2n+1}$O— linear alkoxyl group with n carbon atoms
—V —CH=$CH_2$
V— $CH_2$=CH—
—V1 —CH=CH—$CH_3$
1V— $CH_3$—CH=CH—
-2V —$CH_2$—$CH_2$—CH=$CH_3$
V2- $CH_3$=CH—$CH_2$—$CH_2$—
-2V1 —$CH_2$—$CH_2$—CH=CH—$CH_3$
1V2- $CH_3$—CH=CH—$CH_2$—$CH_2$—
(Linking Group)
—CF2O— —$CF_2$—O—
—OCF2- —O—$CF_2$—
-1O— —$CH_2$—O—
—O1- —O—$CH_2$—
—COO— —COO—
-2- —$CH_2$—$CH_2$—
(Ring Structure)

[Chem. 53]

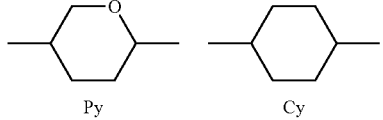

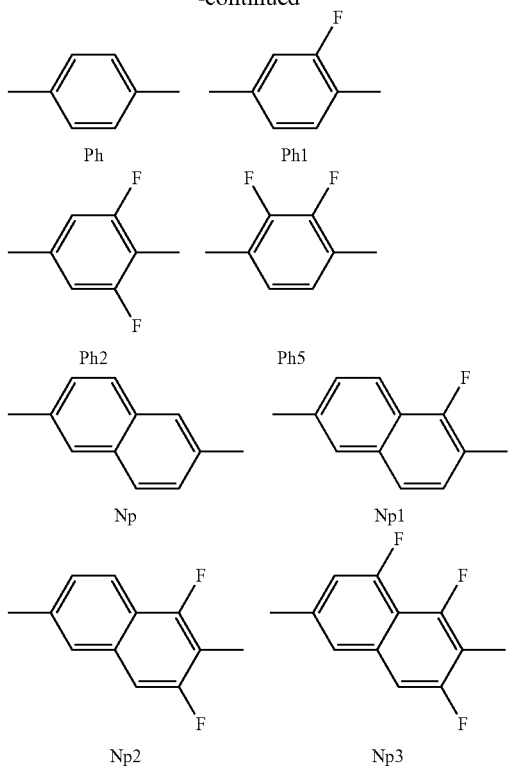

In the examples, the measured characteristics are as follows.
$T_{NI}$: nematic phase-isotropic liquid phase transition temperature (° C.)
Δn: refractive index anisotropy at 25° C.
Δε: dielectric anisotropy at 25° C.
η: viscosity at 25° C. (mPa·s)
$γ_1$: rotational viscosity at 25° C. (mPa·s)
$K_{33}$: elastic constant $K_{33}$ (pN) at 25° C.

(Example 1) Production of 4-methyl-4'-[2-(4-methylphenyl)-1-ethyl]biphenyl(1-Ph-Ph-2-Ph-1)

[Chem. 54]

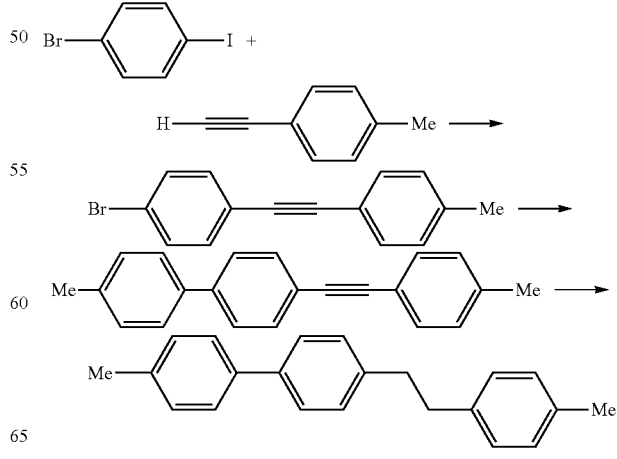

(1-1) In a dry nitrogen atmosphere, 4-iodobromobenzene (55.0 g), copper iodide (I) (1.36 g), tetrakis(triphenylphosphine) palladium (0) (4.13 g), DMF (200 mL), and triethylamine (100 mL) were mixed and heated to 75° C. Under heating, a solution of 4-methylphenylacetylene (24.8 g) dissolved in DMF (100 mL) was added dropwise thereto and then the mixture was further stirred for 3 hours. After the reaction solution was cooled to room temperature, water (200 mL) and toluene (200 mL) were added to form separated layers. The organic layer was washed twice with saturated brine (200 mL) and then dried over anhydrous sodium sulfate. The sodium sulfate was filtered, and the filtrate was concentrated under reduced pressure and then purified by silica gel column chromatography. Furthermore, 4-bromo-4'-methyltran (50.0 g) was obtained by recrystallization with a mixed solvent of acetone and toluene.

(1-2) In a dry nitrogen atmosphere, 4-bromo-4'-methyltran (20.0 g) obtained in the step (1-1), tetrakis(triphenylphosphine) palladium (0) (0.52 g), THF (100 mL), and 2 mol/L potassium carbonate aqueous solution (75 mL) were mixed and heated to 60° C. Under heating, a solution of 4-methylphenylboronic acid (11.0 g) dissolved in THF (25 mL) was added dropwise thereto and then the mixture was further stirred for 2 hours. After cooling the reaction solution with ice, water (400 mL) was added to precipitate the target compound. After filtering the target compound. 4-(4-methylphenyl)-4'-methyltran (21.3 g) was obtained by purification by silica gel column chromatography.

(1-3) 4-(4-methylphenyl)-4'-methyltran (21.3 g) obtained in the step (1-2), 5 wt % palladium carbon (hydrated product) (1.1 g), and THF (300 mL) were placed in an autoclave reactor and stirred in a hydrogen atmosphere (0.5 MPa) at room temperature for 2 hours. The reaction solution was filtered to remove the palladium catalyst and then concentrated under reduced pressure. The obtained residue was purified by silica gel column chromatography and then 15.8 g of 4-methyl-4'-[2-(4-methylphenyl)-1-ethyl] biphenyl was obtained by recrystallization with a mixed solvent of toluene and acetone.

Phase transition temperature (° C.): Cr 120 (N 112) Iso
MS m/z: 286 [M$^+$]
$^1$H NMR (CDCl$_3$, TMS internal standard) δ (ppm)=7.50 (4H, t, J=6.84 Hz), 7.26 (4H, t, J=6.44 Hz), 7.12 (4H, s), 2.92 (4H, s), 2.39 (3H, s), 2.33 (1H, s)

(Example 2) Production of 4-ethyl-4'-[2-(4-propylphenyl)-1-ethyl]biphenyl(2-Ph-Ph-2-Ph-3)

[Chem. 55]

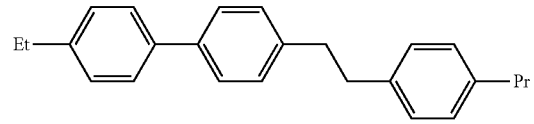

4-ethyl-4'-[2-(4-propylphenyl)-1-ethyl] biphenyl (2-Ph-Ph-2-Ph-3) was produced in the same manner as the method described in Example 1.

Phase transition temperature (° C.): Cr 88 SmX 121 Iso
MS m/z: 328 [M$^+$]
$^1$HNMR (CDCl$_3$, TMS internal standard) δ (ppm)=7.51 (2H, dd, J$_1$=1.88 Hz, J$_{2=8.28}$ Hz), 7.26 (4H, dd, J$_1$=3.16 Hz, J$_2$=8.14 Hz), 7.13 (4H, d, J=4.60 Hz), 2.95 (4H, s), 2.69 (2H, q, J=7.60 Hz), 2.56 (2H, t, J=7.52 Hz, 1.63 (2H, sex, J=7.56 Hz), 1.28 (3H, t, J=7.56 Hz), 0.94 (3H, t, J=7.32 Hz)

Comparative Example 1, Example 3, and Example 4

With respect to Comparative Example 1 (LC-1), liquid crystal compositions of Example 3 (EX-3) containing "1-Ph-Ph-2-Ph-1" produced in Example 1 and Example 4 (EX-4) in which the value of T$_{NI}$ was adjusted so as to be higher than that of Example 3 were prepared, and the physical property values thereof were measured. The composition of the liquid crystal composition and the results of the physical property values are as shown in Table 1.

TABLE 1

|  |  | Comparative Example 1 LC-1 | Example 3 EX-3 | Example 4 EX-4 |
| --- | --- | --- | --- | --- |
| 3-Cy-Cy-V1 |  | 12 | 12 | 12 |
| 3-Cy-Cy-2 |  | 20 | 20 | 22 |
| 3-Cy-Cy-4 |  | 4 | 4 | 2 |
| 3-Ph—Ph-1 |  | 10 | 10 | 8 |
| 3-Cy-Cy-Ph-1 |  |  |  | 2 |
| 3-Cy-Ph—Ph-2 |  | 8 |  |  |
| 1-Ph—Ph-2-Ph-1 | General Formula (ia-1) |  | 8 | 8 |
| 3-Cy-1O—Ph5—O2 |  | 11 | 11 | 11 |
| 2-Cy-Cy-1O—Ph5—O2 |  | 11 | 11 | 11 |
| 3-Cy-Cy-1O—Ph5—O2 |  | 11 | 11 | 11 |
| 1V-Cy-Cy-1O—Ph5—O2 |  | 8 | 8 | 8 |
| 3-Ph-2-Ph—Ph5—O2 |  | 5 | 5 | 5 |
| Total |  | 100 | 100 | 100 |
| T$_{NI}$ [° C.] |  | 76.2 | 72.7 | 75.7 |
| Δn |  | 0.096 | 0.100 | 0.099 |
| γ$_1$ [mPa · s] |  | 93 | 85 | 91 |
| Δε |  | −3.1 | −3.1 | −3.1 |
| K33 [pN] |  | 15.2 | 16.2 | 16.8 |
| γ1/K33 |  | 6.1 | 5.2 | 5.4 |

In Examples 3 and 4 containing "1-Ph-Ph-2-Ph-1" which is a compound represented by General Formula (ia-1), since Δn was large in comparison with Comparative Example 1 and γ₁/K₃₃ was remarkably small, the examples were confirmed to be extremely useful as a liquid crystal composition for a high-speed response television. In addition, it was confirmed that it is possible to obtain a high VHR in Example 3 and Example 4. Here, it was confirmed that there were no display defects such as drop marks, burn-in, or display unevenness in the liquid crystal display elements using these Examples. Here, a drop mark refers to a phenomenon in which a trace formed by dropping the liquid crystal composition appears in white in a case of displaying black, and drop marks occur when carrying out a one drop fill (ODF) method as a method for injecting a liquid crystal composition into a substrate at the time of producing a liquid crystal display element. Furthermore, when PSA liquid crystal display elements were produced by adding 3,500 ppm of Formula (IV-11-MM) as the polymerizable compound represented by General Formula (IV) to the liquid crystal compositions of Example 3 and Example 4, it was confirmed that a good alignment state was obtained, there were no display defects such as drop marks, burn-in, or display unevenness, and the transmittance was high and the response was fast.

[Chem. 56]

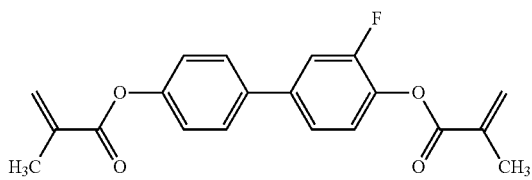

IV-11-MM

When 50 ppm of the antioxidant represented by Formula (H-14) was added to these polymerizable liquid crystal compositions, it was confirmed that a good alignment state was obtained, and in addition to a high transmittance and a high-speed response, the VHR was even higher. Furthermore, when a PSA liquid crystal display element was produced by adding 4,000 ppm of Formula (M302) as a polymerizable compound to the liquid crystal compositions of Example 3 and Example 4, it was confirmed that a good alignment state was obtained, there were no display defects such as drop marks, burn-in, or display unevenness, and the transmittance was high and the response was fast.

[Chem. 57]

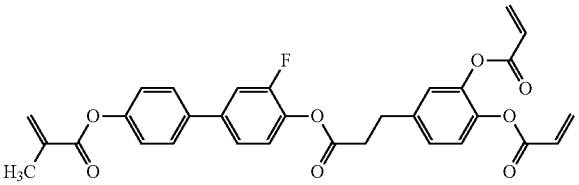

M302

When 100 ppm of the antioxidant represented by Formula (H-14):

[Chem. 58]

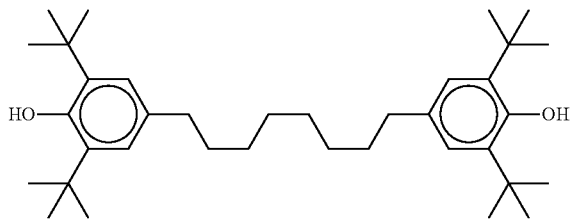

(H-14)

was added to these polymerizable liquid crystal compositions, it was confirmed that a good alignment state was obtained, and there were no display defects such as drop marks, burn-in, or display unevenness, and that in addition to a high transmittance and a high-speed response, the VHR was even higher. When a PSA liquid crystal display element was produced by adding 2,000 ppm of Formula (M302) as the polymerizable compound and 2,000 ppm of Formula (IV-11-MM) to the liquid crystal compositions of Example 3 and Example 4, it was confirmed that a good alignment state was obtained and the transmittance was high and the response was fast. When an antioxidant represented by Formula (H-14) was added to these polymerizable liquid crystal compositions in an amount of 60 ppm, it was confirmed that a good alignment state was obtained, and there were no display defects such as drop marks, burn-in, or display unevenness, and in addition to a high transmittance and a high-speed response, the VHR was even higher.

Example 5, Example 6, Example 7 and Example 8

Liquid crystal compositions of Example 5 (EX-5), Example 6 (EX-6), Example 7 (EX-7), and Example 8 (EX-8) containing the compounds of General Formula (ia-1) and/or General Formula (ib-1) and/or General Formula (ib-2) were prepared and the physical property values thereof were measured. The composition of the liquid crystal compositions and the results of the physical property values are shown in Table 2.

TABLE 2

|  |  | Example 5 EX-5 | Example 6 EX-6 | Example 7 EX-7 | Example 8 EX-8 |
| --- | --- | --- | --- | --- | --- |
| 3-Cy-Cy-V1 |  |  | 6 |  |  |
| 3-Cy-Cy-V |  | 35 | 40 | 40 | 40 |
| 3-Ph—Ph-1 |  | 8 | 7 | 7 |  |
| 1-Ph—Ph-2-Ph-1 | General Formula (ia-1) | 6 | 6 | 6 | 4 |
| 3-Ph—Ph-2-Ph-1 | General Formula (ia-1) |  |  |  | 4 |
| 3-Cy-Ph1—Ph-2-Ph-1 | General Formula (ib-1) |  |  |  | 4 |
| 1-Ph—Ph1—Ph-2-Ph-1 | General Formula (ib-2) |  |  | 2 |  |
| 3-Cy-Ph1—Ph-2-Ph-3 | General Formula (ib-1) |  | 4 | 2 | 4 |

TABLE 2-continued

|  | Example 5 EX-5 | Example 6 EX-6 | Example 7 EX-7 | Example 8 EX-8 |
|---|---|---|---|---|
| 3-Cy-Ph5—O2 |  |  |  | 12 |
| 3-Cy-1O—Ph5—O2 | 7 | 7 | 7 | 7 |
| 2-Cy-Cy-1O—Ph5—O2 | 11 | 11 | 8 |  |
| 3-Cy-Cy-1O—Ph5—O2 | 11 | 11 | 12 | 10 |
| 1V-Cy-Cy-1O—Ph5—O2 | 6 | 6 | 6 | 8 |
| 3-Cy-Ph—Ph5—O2 |  |  | 6 | 3 |
| 1-Ph-2-Ph—Ph5—O2 |  |  |  | 4 |
| 2-Ph-2-Ph—Ph5—O2 | 5 | 4 |  |  |
| 3-Ph-2-Ph—Ph5—O2 | 5 | 4 | 4 |  |
| Total | 100 | 100 | 100 | 100 |
| $T_{NI}$ [° C.] | 73.1 | 76.4 | 80.3 | 77 |
| Δn | 0.100 | 0.101 | 0.103 | 0.100 |
| $\gamma_1$ [mPa · s] | 75 | 77 | 83 | 84 |
| Δε | −2.7 | −2.7 | −2.6 | −2.7 |
| K33 [pN] | 15.6 | 15.9 | 16.9 | 17 |
| γ1/K33 | 4.8 | 4.9 | 4.9 | 4.9 |

These liquid crystal compositions were confirmed to be extremely useful as liquid crystal compositions for fast response televisions, because Δn was large and $\gamma_1/K_{33}$ was remarkably small. In practice, a VA type liquid crystal display element was produced, and it was confirmed that there were no display defects such as drop marks, burn-in, or display unevenness. At the time of measuring the response speed, a high-speed response of 3.7 msec was obtained when the cell thickness was 3.4 μm. Similar results were obtained also in a case where the PSA liquid crystal display element was formed in the same manner as in Example 3 and Example 4.

Example 9

A liquid crystal composition of Example 9 (EX-9) containing the compound of General Formula (ia-1) and the compound of General Formula (ib-1) was prepared and the physical property values thereof were measured. The composition of the liquid crystal composition and the results of the physical property values are shown in Table 3.

TABLE 3

|  |  | Example 9 EX-9 |
|---|---|---|
| 3-Cy-Cy-V |  | 30 |
| 1-Ph—Ph-2-Ph-1 | General Formula (ia-1) | 4 |
| 3-Ph—Ph-2-Ph-1 | General Formula (ia-1) | 4 |
| 3-Cy-Ph1—Ph-2-Ph-1 | General Formula (ib-1) | 3 |
| 3-Cy-Ph1—Ph-2-Ph-2 | General Formula (ib-1) | 2 |
| 3-Cy-Ph1—Ph-2-Ph-3 | General Formula (ib-1) | 3 |
| 3-Ph—Ph5—O2 |  | 14 |
| 3-Cy-Cy-1O—Ph5—O2 |  | 14 |

TABLE 3-continued

|  | Example 9 EX-9 |
|---|---|
| 1V-Cy-Cy-1O—Ph5—O2 | 8 |
| 3-Cy-Cy-Ph5—O2 | 8 |
| 2-Cy-Ph—Ph5—O2 | 5 |
| 3-Cy-Ph—Ph5—O2 | 5 |
| Total | 100 |
| $T_{NI}$ [° C.] | 81.2 |
| $T_{CN}$ [° C.] | G-50 |
| Δn | 0.116 |
| $\gamma_1$ [mPa · s] | 103 |
| Δε | −3.3 |
| K33 [pN] | 16.8 |
| γ1/K33 | 6.1 |

These liquid crystal compositions were confirmed to be extremely useful as liquid crystal compositions for fast response televisions since Δn was large and $\gamma_1/K_{33}$ was remarkably small. In practice, when a VA-type liquid crystal display element was produced and the response speed was measured, a high-speed response of 3.2 msec was obtained when the cell thickness was 2.9 μm. In addition, similarly excellent electrooptical characteristics were obtained even in the case of forming an FFS type liquid crystal display element.

Example 10 and Example 11

The liquid crystal compositions of Example 10 (EX-10) and Example 11 (EX-11) containing the compound of General Formula (ia-1) were prepared and the physical property values thereof were measured. The composition of the liquid crystal compositions and the results of physical property values thereof are shown in Table 4.

TABLE 4

|  |  | Example 10 EX-10 | Example 11 EX-11 |
|---|---|---|---|
| 3-Cy-Cy-V1 |  | 12 | 12 |
| 3-Cy-Cy-2 |  | 20 | 20 |
| 3-Cy-Cy-4 |  | 4 | 4 |
| 3-Ph—Ph-1 |  | 10 | 10 |
| 1-Ph—Ph-2-Ph-1 | General Formula (ia-1) | 8 |  |
| 3-Ph—Ph-2-Ph-1 | General Formula (ia-1) |  | 8 |
| 3-Cy-1O—Ph5—O2 |  | 11 | 11 |
| 2-Cy-Cy-1O—Ph5—O2 |  | 11 | 11 |
| 3-Cy-Cy-1O—Ph5—O2 |  | 11 | 11 |

TABLE 4-continued

|  | Example 10 EX-10 | Example 11 EX-11 |
|---|---|---|
| 1V-Cy-Cy-1O—Ph5—O2 | 8 | 8 |
| 3-Ph-2-Ph—Ph5—O2 | 5 | 5 |
| Total | 100 | 100 |
| $T_{NI}$ [° C.] | 72.7 | 72.2 |
| $\Delta n$ | 0.100 | 0.099 |
| $\gamma_1$ [mPa·s] | 86 | 90 |
| $\Delta\varepsilon$ | −3.1 | −3.1 |
| K33 [pN] | 16.1 | 15.7 |
| γ1/K33 | 5.3 | 5.7 |

These liquid crystal compositions were confirmed to be extremely useful as liquid crystal compositions for fast response televisions since $\Delta n$ was large and $\gamma_1/K_{33}$ was remarkably small. In particular, it was confirmed that in Example 10 using 1-Ph-Ph-2-Ph-1, $\gamma_1/K_{33}$ was reduced by approximately 10% with respect to the value of Example 11. In practice, when a VA-type liquid crystal display element was produced using the liquid crystal compositions of EC-10 and EX-11 and the response speed was measured, high-speed responses of 3.2 msec and 3.5 msec were obtained when the cell thickness was 3.15 μm. In addition, similarly excellent electrooptical characteristics were obtained even in the case of forming an FFS type liquid crystal display element.

Comparative Examples 2 and 3 and Examples 12 and 13

With respect to Comparative Example 2 (LC 2) and Comparative Example 3 (LC 3), the liquid crystal compositions of Examples 12 and 13 containing General Formula (ib-1) and General Formula (ib-2) were prepared and the physical property values thereof were measured. The composition of the liquid crystal compositions and the results of the physical property values thereof are shown in Table 3.

In Example 12 containing General Formula (ib-1) and General Formula (ib-2), the $T_{NI}$ was higher and $\Delta n$ was larger than in Comparative Example 2. Similarly, in Example 13 containing General Formula (ib-1) and General Formula (ib-2), the $T_{NI}$ was higher and the $\Delta n$ was larger than in Comparative Example 3. In addition, it was confirmed that a high VHR was obtained in Example 12 and Example 13. The liquid crystal display element using the liquid crystal compositions of Example 12 and Example 13 was confirmed to have no display defects such as drop marks, burn-in, or display unevenness. From the above, the liquid crystal composition of the present invention has a negative dielectric anisotropy ($\Delta\varepsilon$) with well-balanced characteristics such as a large refractive index anisotropy ($\Delta n$), a low rotational viscosity ($\gamma_1$), a large elastic constant ($K_{33}$), and a high voltage holding ratio (VHR), and the liquid crystal display element using the liquid crystal composition was confirmed to have an excellent response speed with excellent display quality in which display defects such as drop marks, burn-in and display unevenness are absent or suppressed.

The invention claimed is:

1. A liquid crystal composition having negative dielectric anisotropy, comprising
at least one compound represented by General Formula (i):

TABLE 5

|  |  | Comparative Example 2 LC-2 | Example 12 EX-12 | Comparative Example 3 LC-3 | Example 13 EX-13 |
|---|---|---|---|---|---|
| 3-Cy-Cy-2 |  | 15 | 15 | 15 | 15 |
| 3-Cy-Cy-4 |  | 5 | 5 | 5 | 5 |
| 3-Cy-Cy-5 |  | 5 | 5 | 5 | 5 |
| 3-Ph—Ph-1 |  | 5 | 5 | 5 | 5 |
| 3-Cy-Cy-Ph-1 |  | 7 | 7 | 3 | 3 |
| 3-Cy-Ph—Ph-2 |  | 6 | 2 | 8 | 4 |
| 5-Cy-Ph—Ph-2 |  | 6 | 2 | 8 | 4 |
| 3-Cy-Ph1—Ph-2-Ph-1 | General Formula (ib-1) |  | 4 |  | 4 |
| 2-Ph—Ph1—Ph-2-Fh-3 | General Formula (ib-2) |  | 4 |  | 4 |
| 3-Cy-1O—Ph5—O1 |  | 6 | 6 | 6 | 6 |
| 3-Cy-1O—Ph5—O2 |  | 6 | 6 | 6 | 6 |
| 2-Cy-Cy-1O—Ph5—O2 |  | 11 | 11 | 11 | 11 |
| 3-Cy-Cy-1O—Ph5—O2 |  | 11 | 11 | 11 | 11 |
| 1V-Cy-Cy-1O—Ph5—O2 |  | 5 | 5 | 5 | 5 |
| 3-Cy-Ph—Ph5—O3 |  | 6 | 6 | 6 | 6 |
| 3-Cy-Ph—Ph5—O4 |  | 6 | 6 | 6 | 6 |
| Total |  | 100 | 100 | 100 | 100 |
| $T_{NI}$ [° C.] |  | 96.2 | 100.0 | 95.4 | 99.4 |
| $\Delta n$ |  | 0.103 | 0.108 | 0.106 | 0.111 |
| $\gamma_1$ [mPa·s] |  | 141 | 163 | 134 | 158 |
| $\Delta\varepsilon$ |  | −3.5 | −3.6 | −3.4 | −3.5 |

(i)

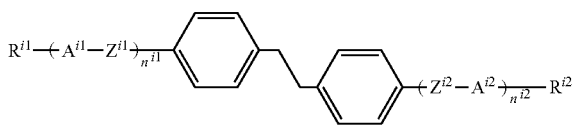

wherein $R^{i1}$ and $R^{i2}$ each independently represent an alkyl group having 1 to 10 carbon atoms, one or two or more non-adjacent —$CH_2$— in $R^{i1}$ and $R^{i2}$ may each independently be substituted with —CH=CH—, —C≡—, —O—, —S—, —COO—, —OCO—, or —CO—, and one or two or more of the hydrogen atoms present in $R^{i1}$ and $R^{i2}$ may each independently be substituted with a fluorine atom or a chlorine atom;

$A^{i1}$ and $A^{i2}$ each independently represent a group selected from a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group;

$Z^{i1}$ and $Z^{i2}$ are each independently a single bond, —$CH_2CH_2$—, —$(CH_2)_4$—, —$OCH_2$—, —$CH_2O$—, —COO—, —OCO—, —$OCF_2$—, —$CF_2O$—, —CH=N—N=CH—, —CH=CH—, —CF=CF—, or —C≡C—;

$n^{i1}$ and $n^{i2}$ each independently represent 0, 1 or 2, provided that $n^{i1}+n^{i2}$ is 2 or more; and in a case where $n^{i1}$ is 2 and therefore plural $A^{i1}$'s and plural $Z^{i1}$'s are present, plural $A^{i1}$'s may be the same or different and plural $Z^{i1}$'s may be the same or different, and in a case where $n^{i2}$ is 2 and therefore plural $A^{i2}$'s and plural $Z^{i2}$'s are present, plural $A^{i2}$'s may be the same or different and plural $Z^{i2}$'s may be the same or different.

2. The liquid crystal composition according to claim 1, wherein, in General Formula (i), $R^{i2}$ is a methyl group.

3. The liquid crystal composition according to claim 1, wherein, in General Formula (i), $A^{i1}$ and $A^{i2}$ are each independently a group selected from a trans-1,4-cyclohexylene group, a 1,4-phenylene group, a 2-fluoro-1,4-phenylene group, or a 3-fluoro-1,4-phenylene group.

4. The liquid crystal composition according to claim 1, wherein, in General Formula (i), $n^{i1}$ is 2, and $n^{i2}$ is 0.

5. The liquid crystal composition according to claim 1, further comprising:

at least one compound selected from compounds represented by General Formulas (N-1), (N-2), or (N-3):

(N-1)

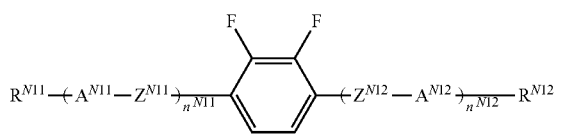

(N-2)

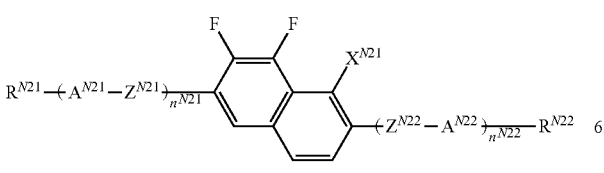

(N-3)

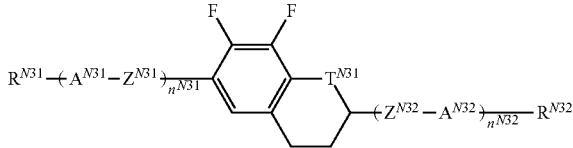

wherein $R^{N11}$, $R^{N12}$, $R^{N21}$, $R^{N22}$, $R^{N31}$, and $R^{N32}$ each independently represent an alkyl group having 1 to 10 carbon atoms, and one or two or more non-adjacent —$CH_2$— in the alkyl group may each independently be substituted with —CH=CH—, —C≡—, —O—, —S—, —CO—, —COO—, or —OCO—;

$A^{N11}$, $A^{N12}$, $A^{N21}$, $A^{N22}$, $A^{N31}$, and $A^{N32}$ each independently represent a group selected from the group consisting of:

(a) a 1,4-cyclohexylene group (one —$CH_2$— or two or more non-adjacent —$CH_2$— present in this group may be substituted with —O—)

(b) a 1,4-phenylene group (one —CH= or two or more non-adjacent —CH= present in this group may be substituted with —N=), (c) a naphthalene-2,6-diyl group, a 1,2,3,4-tetrahydronaphthalene-2,6-diyl group, or a decahydronaphthalene-2,6-diyl group (one —CH= or two or more non-adjacent —CH= present in the naphthalene-2,6-diyl group or the 1,2,3,4-tetrahydronaphthalene-2,6-diyl group may be substituted with —N=), and the group (a), the group (b), and the group (c) may each independently be substituted with a cyano group, a fluorine atom, or a chlorine atom;

$Z^{N11}$, $Z^{N12}$, $Z^{N21}$, $Z^{N22}$, $Z^{N31}$, and $Z^{N32}$ each independently represent a single bond, —$CH_2CH_2$—, —$(CH_2)_4$—, —$OCH_2$—, —$CH_2O$—, —COO—, —OCO—, —$OCF_2$—, —$CF_2O$—, —CH=N—N=CH—, —CH=CH—, —CF=CF—, or —C≡C—;

$X^{N21}$ represents a hydrogen atom or a fluorine atom;

$T^{N31}$ represents —$CH_2$— or an oxygen atom;

$n^{N11}$, $n^{N12}$, $n^{N21}$, $n^{N22}$, $n^{N31}$, and $n^{N32}$ independently represent 0, 1, 2, or 3, provided that $n^{N11}+n^{N12}$, $n^{N21}+n^{N22}$, and $n^{N31}+n^{N32}$ are each independently 1, 2, or 3; and in a case where $n^{N11}$ and/or $n^{N12}$ is 2 or 3 and a plurality with respect to each of $A^{N11}$, $A^{N12}$, $Z^{N11}$, and $Z^{N12}$, is present, the groups or bonds may be the same or different, in a case where $n^{N21}$ and/or $n^{N22}$ is 2 or 3 and a plurality with respect to $A^{N21}$, $A^{N22}$, $Z^{N21}$, and $Z^{N22}$, the groups or bonds may be the same or different, and in a case where $n^{N31}$ and/or $n^{N32}$ is 2 or 3 and a plurality with respect to each of $A^{N31}$, $A^{N32}$, $Z^{N31}$, and $Z^{N32}$ is present, the plural groups or bonds may be the same or different.

6. The liquid crystal composition according to claim 5, wherein, in General Formula (N-1), $A^{N11}$ is a trans 1,4-cyclohexylene group, a 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, $Z^{N11}$ is —OCH$_2$—, —CH$_2$O—, —CF$_2$O—, —OCF$_2$—, —CH$_2$CH$_2$—, —CF$_2$CF$_2$—, or a single bond, n$^{N11}$ is 1, 2, or 3, and n$^{N12}$ is 0.

7. The liquid crystal composition according to claim 5, wherein, in General Formula (N-1), A$^{N11}$ and A$^{N12}$ are a trans 1,4-cyclohexylene group, a 1,4-phenylene group, a 2-fluoro-1,4-phenylene group, a 3-fluoro-1,4-phenylene group, 3,5-difluoro-1,4-phenylene group, 2,3-difluoro-1,4-phenylene group, 1,4-cyclohexenylene group, 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, Z$^{N11}$ and Z$^{N12}$ are —OCH$_2$—, —CH$_2$O—, —CF$_2$O—, —OCF$_2$—, —CH$_2$CH$_2$—, —CF$_2$CF$_2$—, or a single bond, and n$^{N11}$ and n$^{N12}$ each are 1 or 2.

8. The liquid crystal composition according to claim 5, wherein the total content of General Formulas (N-1), (N-2), and (N-3) is from 10% to 90% by mass.

9. The liquid crystal composition according to claim 1, further comprising:
at least one compound selected from compounds represented by General Formula (L):

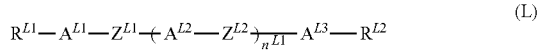
(L)

wherein R$^{L1}$ and R$^{L2}$ each independently represent an alkyl group having 1 to 10 carbon atoms, and one or two or more non-adjacent —CH$_2$— in the alkyl group may each independently be substituted with —CH=CH—, —O—, —CO—, —COO—, or —OCO—;

n$^{L1}$ represents 0, 1, 2, or 3;

A$^{L1}$, A$^{L2}$, and A$^{L3}$ each independently represent a group selected from the group consisting of:
(a) a 1,4-cyclohexylene group (one —CH$_2$— or two or more non-adjacent —CH$_2$— present in this group may be substituted with —O—),
(b) a 1,4-phenylene group (one —CH= or two or more non-adjacent —CH= present in this group may be substituted with —N=),
(c) a naphthalene-2,6-diyl group, a 1,2,3,4-tetrahydronaphthalene-2,6-diyl group, or a decahydronaphthalene-2,6-diyl group (one —CH= or two or more non-adjacent —CH= present in the naphthalene-2,6-diyl group or the 1,2,3,4-tetrahydronaphthalene-2,6-diyl group may be substituted with —N=), and
the group (a), the group (b), and the group (c) may each independently be substituted with a cyano group, a fluorine atom, or a chlorine atom;

Z$^{L1}$ and Z$^{L2}$ each independently represent a single bond, —CH$_2$CH$_2$—, —(CH$_2$)$_4$—, —OCH$_2$—, —CH$_2$O—, —COO—, —OCO—, —OCF$_2$—, —CF$_2$O—, —CH=N—N=CH—, —CH=CH—, —CF=CF—, or —C≡C—; and in a case where n$^{L1}$ is 2 or 3 and plural A$^{L2}$'s are present, these may be the same or different, and in a case where n$^{L1}$ is 2 or 3 and plural Z$^{L2}$'s are present, these may be the same or different, provided that compounds represented by General Formula (i), and compounds represented by General Formula (N-1), General Formula (N-2), and General Formula (N-3) are excluded.

10. The liquid crystal composition according to claim 1, further comprising:
at least one polymerizable compound.

11. The liquid crystal composition according to claim 1, wherein a dielectric anisotropy (Δε) at 25° C. is from −2.0 to −8.0,
a refractive index anisotropy (Δn) at 25° C. is from 0.08 to 0.14,
a viscosity (η) at 25° C. is from 10 to 50 mPa·s,
a rotational viscosity (γ$_1$) at 25° C. is from 60 to 2,000 mPa·s,
a nematic phase-isotropic liquid phase transition temperature (T$_{NI}$) is from 60° C. to 120° C., and
an elastic constant (K$_{33}$) is from 10.0 to 20.0.

12. A liquid crystal display element, comprising the liquid crystal composition according to claim 1.

13. A liquid crystal display element for active matrix driving, comprising the liquid crystal composition according to claim 1.

14. A liquid crystal display element for VA mode, PSA mode, PSVA mode, IPS mode, FFS mode or ECB mode, comprising the liquid crystal composition according to claim 1.

15. The liquid crystal composition according to claim 1, further comprising:
at least one compound selected from a compound represented by General Formula (II-A1) and General Formula (II-A3):

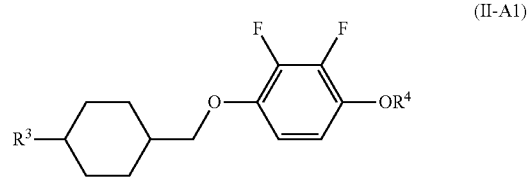
(II-A1)

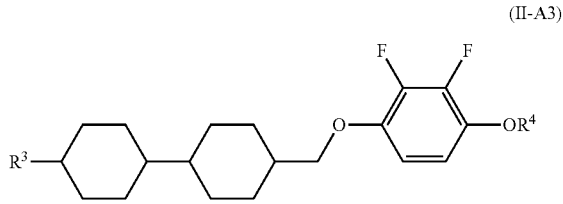
(II-A3)

wherein R$^3$ and R$^4$ each independently represent an alkyl group having 1 to 5 carbon atoms or an alkenyl group having 2 to 5 carbon atoms, and
the total content of the compound represented by General Formula (i) is 8% or more, and the total content of the compound represented by General Formula (II-A1) and (II-A3) is 20% or more with respect to the total amount of the composition.

* * * * *